US011904054B2

(12) United States Patent
Mansour et al.

(10) Patent No.: US 11,904,054 B2
(45) Date of Patent: Feb. 20, 2024

(54) COMPOSITIONS AND METHODS FOR DELIVERING PHARMACEUTICAL AGENTS

(71) Applicant: Arizona Board of Regents on Behalf of the University of Arizona, Tucson, AZ (US)

(72) Inventors: Heidi M. Mansour, Tucson, AZ (US); Stephen Black, Tucson, AZ (US); Maria Acosta, Tucson, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 0 days.

(21) Appl. No.: 16/963,043

(22) PCT Filed: Jan. 18, 2019

(86) PCT No.: PCT/US2019/014255
§ 371 (c)(1),
(2) Date: Jul. 17, 2020

(87) PCT Pub. No.: WO2019/143981
PCT Pub. Date: Jul. 25, 2019

(65) Prior Publication Data

US 2020/0338007 A1 Oct. 29, 2020

Related U.S. Application Data

(60) Provisional application No. 62/619,326, filed on Jan. 19, 2018.

(51) Int. Cl.

| | |
|---|---|
| ***A61K 9/16*** | (2006.01) |
| ***A61K 9/00*** | (2006.01) |
| ***A61K 9/51*** | (2006.01) |
| ***A61K 31/366*** | (2006.01) |
| *A61K 31/047* | (2006.01) |
| *A61K 31/221* | (2006.01) |
| *A61K 45/06* | (2006.01) |
| *B82Y 5/00* | (2011.01) |

(52) U.S. Cl.
CPC .......... *A61K 9/1682* (2013.01); *A61K 9/0075* (2013.01); *A61K 9/5192* (2013.01); *A61K 31/366* (2013.01); *A61K 31/047* (2013.01); *A61K 31/221* (2013.01); *A61K 45/06* (2013.01); *B82Y 5/00* (2013.01)

(58) Field of Classification Search
CPC .... A61K 31/366; A61K 9/0075; A61K 45/06; A61K 9/1682; A61K 9/5192; B82Y 5/00
See application file for complete search history.

(56) References Cited

U.S. PATENT DOCUMENTS

| | | | | |
|---|---|---|---|---|
| 6,766,799 | B2 | 7/2004 | Edwards | |
| 6,848,197 | B2 | 2/2005 | Chen | |
| 7,278,425 | B2 | 10/2007 | Edwards | |
| 8,197,845 | B2 | 6/2012 | Hartig | |
| 8,496,002 | B2 | 7/2013 | Ellwanger | |
| 2002/0039595 | A1 | 4/2002 | Keller | |
| 2009/0196920 | A1* | 8/2009 | Carminati | A61K 9/5047 424/456 |
| 2011/0021592 | A1* | 1/2011 | Magdassi | A61K 9/5123 514/406 |
| 2011/0064794 | A1 | 3/2011 | Deng et al. | |
| 2015/0065685 | A1 | 3/2015 | Arany | |

FOREIGN PATENT DOCUMENTS

WO WO 2003/103640 12/2003

OTHER PUBLICATIONS

Flanagan, Judith L., Flanagan et al., Nutrition & Metabolism 2010, 7:30 (Year: 2010).*
Bolourchian, N., et al., Iranian Journal of Pharmaceutical Research : IJPR, 2013. 12(Suppl): p. 11-20.
Cooper et al. Enantiomer excesses of rare and common sugar derivatives in carbonaceous meteorites, Proceedings of the National Academy of Sciences of the USA, vol. 113, No. 24, May 31, 2016, p. E3322-E3331.
De Jesus Perez, V.A., Molecular pathogenesis and current pathology of pulmonary hypertension. Heart Fail Rev. May 2016;21(3):239-57.
Gan, C.T., et al., A review of pulmonary arterial hypertension: Part 1. Novel insights and classification. Netherlands Heart Journal, 2004. 12(6): p. 287-294.
Graeser, K.A., et al., Physicochemical Properties and Stability of Two Differently Prepared Amorphous Forms of Simvastatin. Crystal Growth & Design, 2008. 8(1): p. 128-135.
Guilluy, C., et al., RhoA and Rho Kinase Activation in HumanPulmonary Hypertension. Am J Respir Crit Care Med, 2009. 179(12): p. 1151-8.
Haghi, M., et al., Across the pulmonary epithelial barrier: Integration of physicochemical properties and human cell models to study pulmonary drug formulations. Pharmacol Ther, 815 2014. 144(3): p. 235-52.
Hayes, et al., Improvement of Sinus Disease in Cystic Fibrosis with Ivacaftor Therapy. Am J Respir Crit Care Med. Aug. 15, 2014;190(4):468.
Hill, NS, et al., Inhaled Therapies for Pulmonary Hypertension. Respiratory care. 2015;60(6):794-805.
International Search Report & Written Opinion, International Application No. PCT/US2019/014255, dated Apr. 11, 2019, 9 pages.
Iqbal, M., et al., Lung Mitochondrial Dysfunction in Pulmonary Hypertension Syndrome. II. Oxidative Stress and Inability to Improve Function with Repeated Additions of Adenosine Diphosphate. Poult Sci, 2001. 80(5): p. 656-65.
Jain, et al., Spray Drying in Pharmaceutical Industry: A Review. Research J. Pharma. Dosage Forms and Tech. 2011; 4(2): 74-79.

(Continued)

*Primary Examiner* — Andrew S Rosenthal
*Assistant Examiner* — Lyndsey M Beckhardt
(74) *Attorney, Agent, or Firm* — Casimir Jones, S.C.; Tanya A. Arenson

(57) ABSTRACT

Provided herein are compositions and methods for treating respiratory and pulmonary vascular disease. In particular, provided herein are spray dried simvastatin for delivery to the lung.

9 Claims, 26 Drawing Sheets

(56) References Cited

OTHER PUBLICATIONS

Jun, S.W., et al., Preparation and characterization of simvastatin/hydroxypropyl-b-cyclodextrin inclusion complex using supercritical antisolvent (SAS) process. Journal of Pharmaceutics and Biopharmaceutics, 2007. 66(3): p. 413-421.
Kou et al. Dual targeting of I-carnitine-conjucated nanoparticles to OCTN2 and ATB0, + to deliver chemotherapeutic agents for colon cancer therapy, Drug Delivery, vol. 24, No. 1, Sep. 15, 2017, p. 1338-1349.
Kuhr, FK, et al., New mechanisms of pulmonary arterial hypertension: role of CA2+ signaling. American Journal of Physiology—Heart and Circulatory Physiology. 2012;302(8):H1546-H1562.
Lee, J.H., et al., Simvastatin Inhibits Cigarette Smoking-induced Emphysema and Pulmonary Hypertension in Rat Lungs. Am J Respir Crit Care Med, 2005. 172(8): p. 987-93.
Li, X., et al., Physicochemical characterization and aerosol dispersion performance of organic solution advanced spray-dried microparticulate/ nanoparticulate antibiotic dry powders of tobramycin and azithromycin for pulmonary inhalation aerosol delivery. European Journal of Pharmaceutical Sciences, 2014. 52: p. 191-205.
Li, X., et al., Design, Characterization, and Aerosol Dispersion Performance Modeling of Advanced Spray-Dried Microparticulate/Nanoparticulate Mannitol Powders for Targeted Pulmonary Delivery as Dry Powder Inhalers. J Aerosol Med Pulm Drug Deliv, 2014. 27(2): p. 731 81-93.
Li, X., et al., Design, Characterization, and Aerosol Dispersion Performance Modeling of Advanced Co-Spray Dried Antibiotics with Mannitol as Respirable Microparticles/Nanoparticles for Targeted Pulmonary Delivery as Dry Powder Inhalers. Pharm Sci, 2014. 103(9): p. 2937-49.
Liao, J.K., et al., Rho Kinase (ROCK) Inhibitors. Journal of cardiovascular pharmacology, 2007. 50(1): p. 17-24.
Mansour, HM, et al., Nanomedicine in pulmonary delivery. Int J Nanomedicine. 2009;4:299-319.
Mansour, HM, et al., Lipids in Nanotechnology: American Oil Chemists Society Press, Chicago, Ill; 2011:221-268.
Mathew, B., et al., American Journal of Respiratory Cell and Molecular Biology, 2011. 44(3): p. 415-422.
Meenach, S.A., et al., High-Performing Dry Powder Inhalers of Paclitaxel DPPC/DPPG Lung Surfactant-Mimic Multifunctional Particles in Lung Cancer: Physicochemical Characterization, In Vitro Aerosol Dispersion, and Cellular Studies. AAPS PharmSciTech, 2014. 15(6): p. 1574-87.
Meenach, S.A., et al., Characterization and aerosol dispersion performance of advanced spray-dried chemotherapeutic PEGylated phospholipid particles for dry powder inhalation delivery in lung cancer. European Journal of Pharmaceutical Sciences, 2013. 49(4): p. 699-797.
Muralidharan, P, et al., Inhalable nanoparticulate powders for respiratory delivery. Nanomedicine: Nanotechnology, Biology and Medicine. 2015;11(5):1189-1199.
Muralidharan, P, et al., Inhalable PEGylated Phospholipid Nanocarriers and PEGylated Therapeutics for Respiratory Delivery as Aerosolized Colloidal Dispersions and Dry Powder Inhalers. Pharmaceutics. 2014;6(2):333-353.
Muralidharan, P., et al., Microparticulate/nanoparticulate powders of a novel Nrf2 activator and an aerosol performance enhancer for pulmonary delivery targeting the lung Nrf2/Keap-1 pathway. Mol. Syst. Des. Eng., 2016, 1, 48-65.
Peacock, A., Pulmonary hypertension. Eur Respir Rev, 2013. 22(127): p. 20-5.
Podstawka, E., et al., Food additives characterization by infrared, Raman, and surface-enhanced Raman spectroscopies. Journal of Raman Spectroscopy, 2007. 38(3): p. 356-363.
Rao, M., et al., Dissolution Improvement of Simvastatin by Surface Solid Dispersion Technology. Dissolution Technologies, 2010. 17(2): p. 27-34.
Runo, J.R. et al. Primary pulmonary hypertension. 2003. 361(9368): p. 759 1533-44.
Saeed, et al. Effects of Levo-Carnitine and Simvastatin on Fasting Glucose and C-Reactive Protein Levels in Insulin Resistant Rats, Pakistan Journal of Physiology, vol. 11, No. 3, Sep. 30, 2015, p. 6-9.
Simonneau, G, et al., Updated Clinical Classification of Pulmonary Hypertension. J. Am. Coll Cardiol, 2013; 62(25 Suppl):D34-D41.
Singh, H., B. et al., Preparation, Characterization and Pharmacodynamic Evaluation of Fused Dispersions of Simvastatin using PEO-PPO Block Copolymer. Journal of Pharmaceutical Research: IJPR, 2012. 11(2): p. 433-445.
Stenmark, K, et al., Cellular and Molecular Mechanisms of Pulmonary Vascular Remodeling. Annual Review of Physiology. 1997;59(1):89-144.
Stocke, NA, et al., Formulation and characterization of inhalable magnetic nanocomposite microparticles (MnMs) for targeted pulmonary delivery via spray drying. International journal of pharmaceutics. 2015;479(2):320-328.
Tan, X., et al., The effect of dietary I-carnitine supplementation on pulmonary hypertension syndrome mortality in broilers exposed to low temperatures. Anim Physiol Anim Nutr (Berl), 2008. 92(2): p. 203-10.
Xu, et al., Simvastatin delivery via inhalation attenuates airway inflammation in a murine model of asthma. Int Immunopharmacol, 2012. 12(4): p. 556-64.
Xu, Z, et al., Particle Interactions in Dry Powder Inhaler Unit Processes: A Review. Journal of Adhesion Science and Technology. 2011;25(4-5):451-482.

* cited by examiner

Simvastatin

L-Carnitine

D-mannitol g a b c d e f g g

COMPOSITIONS AND METHODS FOR DELIVERING PHARMACEUTICAL AGENTS

CROSS REFERENCE TO RELATED APPLICATIONS

This application is a U.S. 371 national phase entry of International Patent Application No. PCT/US2019/014255, filed Jan. 18, 2019, which claims priority to and the benefit of U.S. Provisional Application No. 62/619,326, filed Jan. 19, 2018, which are hereby incorporated by reference in their entireties.

STATEMENT REGARDING FEDERALLY SPONSORED RESEARCH OR DEVELOPMENT

This invention was made with government support under Grant Nos. R01 HL060190 and R01 HL137282 awarded by NIH. The government has certain rights in the invention.

FIELD

Provided herein are compositions and methods for treating respiratory and pulmonary vascular disease. In particular, provided herein are spray dried simvastatin and/or L-carnitine for delivery to the lung.

BACKGROUND

Examples of clinically relevant lung disease include pulmonary vascular disease and acute lung injury.

Pulmonary vascular disease relates to any condition that affects the blood vessels along the route between the heart and lungs. Examples include pulmonary arterial hypertension (Increased blood pressure in the pulmonary arteries), pulmonary hypertension (PH), pulmonary venous hypertension (increased blood pressure in the pulmonary veins), and pulmonary embolism (a blood clot breaks off from a deep vein (usually in the leg), travels into the right heart, and is pumped into the lungs).

Pulmonary hypertension (PH) is a life-threatening disease characterized by an increase in pulmonary artery pressure (de Jesus Perez, V. A., Heart Fail Rev, 2015; Gan, C. T., et al., Netherlands Heart Journal, 2004. 12(6): p. 287-294). PH is complex and multifactorial making a challenge to researchers for the understanding of molecular mechanisms that are involved in the pathogenesis and the developing of novel pharmacological strategies to treat this disease.

Pulmonary hypertension (PH) is clinically classified into 5 categories (Simonneau G, et al., J. Am. Coll Cardiol, 2013; 62(25 Suppl):D34-D41): 1) Pulmonary arterial hypertension (PAH), 2) Pulmonary hypertension due to left sided heart disease, 3) Pulmonary hypertension related to lung disease or hypoxia, 4) Chronic thromboembolic pulmonary hypertension, 5) Pulmonary hypertension related to multifactorial mechanisms. Pulmonary arterial hypertension (PAH) is one of the most devastating chronic diseases of the pulmonary circulation. In addition to patients with idiopathic and heritable PAH, PAH can also be found in patients in the setting of collagen vascular disease (e.g., localized cutaneous systemic sclerosis), portal hypertension, congenital left-to-right intracardiac shunts, infections with the human immunodeficiency virus (HIV), and persistent pulmonary hypertension of the newborn (Farber H W, et al., New England Journal of Medicine. 2004; 351(16):1655-1665). Pulmonary hypertension (PH) associated with lung diseases and hypoxia can be encountered by healthy individuals living in high altitude, divers, mountain climber, athletes, and during exercise and rehabilitation (Stenmark K, et al., Annual Review of Physiology. 1997; 59(1):89-144). PH is defined clinically as a mean pulmonary arterial pressure of ≥25 mmHg at rest or ≥30 mmHg during exercise (Hill N S, et al., Respiratory care. 2015; 60(6):794-805; Kuhr F K, et al., American Journal of Physiology-Heart and Circulatory Physiology. 2012; 302(8):H1546-H1562). In patients with PAH and PH associated lung diseases and hypoxia, the increased PAP can be attributed to combined effects of sustained vasoconstriction, concentric vascular remodeling, in situ thrombosis, and arterial wall stiffening, resulting in elevated pulmonary vascular resistance (Kuhr et al., supra). As a consequence, elevated pulmonary vascular resistance increases the right heart afterload and in the fullness of time results in right ventricular hypertrophy and eventually right heart failure and death (Kuhr et al., supra).

The impediment of the ejection of blood by the right ventricle and subsequently the failure of the right heart due to the increase in pulmonary vascular resistance is what makes PH a fatal disease (Runo, J. R. and J. E. Loyd, Lancet, 2003. 361(9368): p. 759 1533-44). In PH, there is an evident interaction between the pulmonary and cardiovascular system. However, that interaction is not well-defined because of the deficiency of arduous investigation as a result of the symptomatic intersection and inadequate diagnostic capability (Hayes et al., American Journal of Respiratory and Critical Care Medicine, 2014. 190).

Additional treatments for lung disease and injury are needed.

SUMMARY

Pulmonary drug delivery of dry powder aerosol offers many advantages such as a large surface area for high drug absorption (Mansour H M, et al., Int J Nanomedicine. 2009; 4:299-319; Muralidharan P, et al., Pharmaceutics. 2014; 6(2):333-353; Muralidharan P, et al., Nanomedicine: Nanotechnology, Biology and Medicine. 2015; 11(5):1189-1199), a rapid onset of therapeutic action (Meenach S A, et al., 2014 supra; Olschewski et al., supra; Tissot et al., supra; Mansour et al., supra; Muralidharan et al., 2014, supra; Muralidharan et al., 2015, supra; Xu Z, et al., Journal of Adhesion Science and Technology. 2011; 25(4-5):451-482), low enzymatic activity (Muralidharan et al., 2014, supra; Muralidharan et al., 2015; Stocke N A, et al., International journal of pharmaceutics. 2015; 479(2):320-328), extensive blood supply (Mansour H M, et al., Lipids in Nanotechnology: American Oil Chemists Society Press, Chicago, Ill.; 2011:221-268), avoidance of first-pass metabolism (Mansour et al., 2009, supra; Muralidharan et al., 2014, supra; Mansour et al., 2011, supra), reduced dosing frequency (Muralidharan et al., 2014, supra;), and reduced side effects (Mansour et al., 2015, supra; Mansour et al., 2011, supra).

However, prior to the present invention, such delivery of simvastatin (Sim) was not possible. Provided herein for the first time is a high-throughput advanced engineering method to develop Sim and Sim co-particles inhalable particles for local delivery to the lungs as DPIs.

For example, in some embodiments, provided herein is a composition, comprising: simvastatin nano or microparticles. In some embodiments, the nano or microparticles further comprise a pharmaceutically acceptable carrier or second active agent. In some embodiments, the pharmaceutically acceptable carrier is a D-mannitol (Man) and the second active agent is L-carnitine (L-Car). In some embodiments, simvastatin and Man or L-Car are present at a molar ratio of 90:10 to 10:90 Sim:Man or L-Car. In some embodiments, the composition is spray dried. In some embodiments, the particles are a dry powder.

In some embodiments, provided herein are L-Car nano or microparticles.

In some embodiments, provided herein are Sim and L-Car nano or microparticles.

In some embodiments, the nano or microparticles are generated by a method, comprising: a) preparing a first solution comprising simvastatin and/or L-Car in an organic solvent and a second solution comprising the pharmaceutically acceptable carrier in an organic solvent; and b) co-spraying the first and second solutions using a spray drying apparatus. In some embodiments, the organic solvent is methanol. In some embodiments, the nano or microparticles are generated by a method, comprising: a) preparing a solution comprising simvastatin and/or L-Car and optionally a pharmaceutically acceptable carrier in an organic solvent; and spraying the solution using a spray drying apparatus.

Additional embodiments provide a system, comprising: the Sim and/or L-Car compositions described herein; and a dry powder inhaler device.

Further embodiments provide a method of treating pulmonary hypertension (PH) or other lung disorders in a subject, comprising: administering the Sim and/or L-Car compositions described herein to a subject diagnosed with or having signs or symptoms of PH, asthma, COPD, acute lung injury, radiation-induced lung injury, etc. under conditions such that the signs or symptoms are reduced. In some embodiments, the method further comprises administering an additional treatment for PH (e.g., including but not limited to, a vasodilator, an anticoagulant, an antiplatelet agent, an anti-inflammatory agent, or a vascular-remodeling therapy). In some embodiments, the composition is administered to the lung of the subject using a dry powder inhaler.

Still further embodiments provide the use of the Sim and/or L-Car compositions described herein to treat PH in a subject diagnosed with or having signs or symptoms of PH.

Yet other embodiments provide the Sim and/or L-Car compositions described herein for use in treating PH in a subject diagnosed with or having signs or symptoms of PH.

Also provided herein is a method of administering Sim and/or L-Car to the lung of a subject, comprising: delivering the Sim and/or L-Car compositions described herein to the lung of a subject using a dry powder inhaler. In some embodiments, the delivering treats PH.

Additional embodiments are described herein.

Figure 1A:
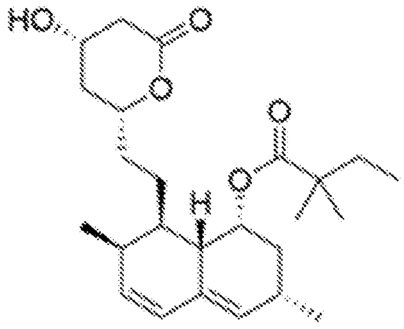
FIG. 1. Chemical structure of: (a) Simvastatin: (b) L-Carnitine: (c) D-mannitol FIG. 2. SEM micrographs of raw and SD particles (magnification 12,000×) for: (a) Raw Sim; (b) Raw L-Car; (c) SD Sim (25% PR); (D) SD Sim (50% PR); (e) SD L-Car (25% PR); (f) SD L-Car (50% PR)

ATR-FTIR spectrum of nanostructured respirable spray-dried particles of simvastatin drug (B); X-ray powder diffractogram of nanostructured respirable spray-dried particles of simvastatin drug (C); and in vivo lamb data by ACh challenge for aerosolized simvastatin after one hour post-simvastatin aerosol treatment (D).

DEFINITIONS

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human or non-human mammal subject.

As used herein, the term "diagnosed," as used herein, refers to the recognition of a disease by its signs and symptoms (e.g., resistance to conventional therapies), or genetic analysis, pathological analysis, histological analysis, and the like.

As used herein, the term "effective amount" refers to the amount of a compound (e.g., a compound of the present disclosure) sufficient to effect beneficial or desired results. An effective amount can be administered in one or more administrations, applications or dosages and is not limited to a particular formulation or administration route.

As used herein, the term "co-administration" refers to the administration of at least two agent(s) (e.g., a compound of the present disclosure) or therapies to a subject. In some embodiments, the co-administration of two or more agents/therapies is concurrent. In some embodiments, a first agent/therapy is administered prior to a second agent/therapy. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

As used herein, the term "pharmaceutical composition" refers to the combination of an active agent with a carrier, inert or active, making the composition especially suitable for diagnostic or therapeutic use in vivo, in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa., (1975)).

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water and industrial samples. Such examples are not however to be construed as limiting the sample types applicable to the present disclosure.

As used herein, the terms "purified" or "to purify" refer, to the removal of undesired components from a sample. As used herein, the term "substantially purified" refers to molecules that are at least 60% free, at least 65% free, at least 70% free, at least 75% free, at least 80% free, at least 85% free, at least 90% free, at least 95% free, at least 96% free, at least 97% free, at least 98% free, at least 99% free, or 100% free from other components with which they usually associated.

As used herein, the term "modulate" refers to the activity of a compound (e.g., a compound of the present disclosure) to affect (e.g., to promote or retard) an aspect of cellular function.

As used herein, the phrase "in need thereof" means that the subject has been identified as having a need for the particular method or treatment. In some embodiments, the identification can be by any means of diagnosis. In any of the methods and treatments described herein, the subject can be in need thereof. In some embodiments, the subject is in an environment or will be traveling to an environment in which a particular disease, disorder, condition, or injury is prevalent.

DETAILED DESCRIPTION

For years, Simvastatin (Sim) which is an inhibitor of 3-hydroxy-3-methyl-3-glutaryl coenzyme A reductase has been used to lower serum cholesterol (Xu et al., Int Immunopharmacol, 2012. 12(4): p. 556-64). However, recent studies have shown this drug has many other pharmacological effects. Sim has a potent anti-proliferative and pro-apoptotic effect on vasculature smooth-muscle cells through the inhibition of the synthesis of isoprenoids intermediates (geranylgeranylpyrophosphate and farnesylpyrophosphate), which are essential for the post-translational isoprenylation of Rho, Rac and Ras family GTPases (intracellular signaling molecules whose proper membrane localization and function are dependent on the lipid character that isoprenoids offer to them) (Guilluy, C., et al., Am J Respir Crit Care Med, 2009. 179(12): p. 1151-8; Liao, J. K., et al., Journal of cardiovascular pharmacology, 2007. 50(1): p. 17-24). Furthermore, Sim has anti-oxidant, anti-inflammatory, anti-thrombotic and immunomodulatory effects through different mechanisms. Some of them have to be with the augmented expression of endothelial nitric oxide synthase (eNOS) via inhibition of the RhoA/Rho kinase pathway which leads to the stabilization of eNOS mRNA and with the inhibition RhoA/Rho kinase pathway which is in charge of the rapid phosphorylation and activation of eNOS through the phosphatidylinositol (PI)-3 kinase/protein kinase Akt pathway (Liao et a., supra). Overall, RhoA/Rho kinase downregulates endothelial function expressing and activating eNOS (Liao et al, supra). With all these effects together, it has been proposed that Sim may ameliorate PH (Xu et al., supra; Peacock, A., Eur Respir Rev, 2013. 22(127): p. 20-5). Other conditions including asthma (Xu et al., supra), COPD (Lee, J. H., et al., Am J Respir Crit Care Med, 2005. 172(8): p. 987-93), acute lung injury, among others, have been treated successfully with Sim and other statins. Likewise, radiation-induced lung injury (RILI) which is associated with increased generation of reactive oxygen and nitrogen species, secretion of inflammatory cytokines and chemokines, and inflammatory cell recruitment into the lung parenchyma, has also been proposed to be treated with Sim due to the property of this drug to attenuate lung injury (as measured by vascular leak), leukocyte infiltration, and the histological evidence to mitigate oxidative stress, as well as the of radiation-induced dysregulated lung gene expression (Mathew, B., et al., American Journal of Respiratory Cell and Molecular Biology, 2011. 44(3): p. 415-422).

L-Carnitine (L-Car) [(4-N-trimethylammonium-3-hydroxybutyric acid)] is a cofactor required for transport of long-chain fatty acids into the inner mitochondrial matrix, where they undergo β-oxidation for cellular energy (ATP) production (Tan, X., et al, Anim Physiol Anim Nutr (Berl), 2008. 92(2): p. 203-10). In addition, studies indicate that L-Car has an anti-peroxidative effect on several tissues, which may account for its beneficial effect in oxidant-induced injury, making L-Car an excellent candidate for PH therapy (Tan et al., supra; Iqbal, M., et al., Poult Sci, 2001. 80(5): p. 656-65).

D-mannitol (Man) is a non-reducing sugar alcohol that exerts mucolytic properties because it is an osmotic agent. Man has also been used as a carrier for dry powder inhalers due to its power to improve in vitro aerosol performance (Li, X., et al., J Aerosol Med Pulm Drug Deliv, 2014. 27(2): p. 731 81-93).

Because of all the possible effects that Sim and L-Car are shown to offer, there is considerable interest in the use of these two compounds for the treatment of PH. In addition, because of the improvement in the in vitro aerosol performance with Man, studies described herein engineered Sim and L-Car and Sim and Man into advanced inhalable dry powders that can be targeted to the respiratory tract as dry powder inhalers (DPIs) using a FDA-approved human DPI device.

Accordingly, provided herein are simvastatin and/or L-Car nano or microparticles. In some embodiments, simvastatin and/or L-Car are present in a dry powder or other form generated by spray drying (See e.g., below and Jain et al., Research J. Pharma. Dosage Forms and Tech. 2011; 4(2): 74-79). In some embodiments, simvastatin is spray dried alone or with a pharmaceutically acceptable carrier. In some embodiments, the pharmaceutically acceptable carrier is a sugar (e.g., D-mannitol, lactose, trehalsose or xylitol). In some embodiments, simvastatin and L-Car are co-spray dried together. In some embodiments, the simvastatin and carrier are present at a molar ratio of 90:10 to 10:90 simvastatin:carrier (e.g., 50:50).

In some embodiments, spray-drying is co-spray drying where the active agent (Sim or L-Car) and a carrier (e.g., Man) or second active agent (e.g., L-Car) are separately dissolved in a solvent and then co-sprayed. In some embodiments, the active agent and second active agent or carrier are mixed prior to spraying and spray dried as a single solution.

Generally, during spray-drying, heat from a hot gas such as heated air or nitrogen is used to evaporate a solvent from droplets formed by atomizing a continuous liquid feed. If desired, the spray drying or other instruments, e.g., jet milling instrument, used to prepare the dry particles can include an inline geometric particle sizer that determines a geometric diameter of the respirable dry particles as they are being produced, and/or an inline aerodynamic particle sizer that determines the aerodynamic diameter of the respirable dry particles as they are being produced.

For spray drying, solutions, emulsions or suspensions that contain the components of the dry particles to be produced in a suitable solvent (e.g., aqueous solvent, organic solvent, aqueous-organic mixture or emulsion) are distributed to a drying vessel via an atomization device. For example, a nozzle or a rotary atomizer may be used to distribute the solution or suspension to the drying vessel. For example, a rotary atomizer having a 4- or 24-vaned wheel may be used. Examples of suitable spray dryers that can be outfitted with either a rotary atomizer or a nozzle, include, Mobile Minor Spray Dryer or the Model PSD-1, both manufactured by GEA Group (Niro, Inc.; Denmark). Actual spray drying conditions will vary depending, in part, on the composition of the spray drying solution or suspension and material flow rates. The person of ordinary skill will be able to determine appropriate conditions based on the compositions of the solution, emulsion or suspension to be spray dried, the desired particle properties and other factors. In general, the inlet temperature to the spray dryer is about 90° C. to about 300° C. The spray dryer outlet temperature will vary depending upon such factors as the feed temperature and the properties of the materials being dried. Generally, the outlet temperature is about 50° C. to about 150° C. The spray dryer outlet temperature will vary depending upon such factors as the feed temperature and the properties of the materials being dried. Generally, the outlet temperature is about 50° C. to about 150° C.

A nitrogen source with a specified moisture level may be flown over, across, or through the dry powder to add a specific moisture content to the dry powder. Such moisture can provide the desired working density of the powder. Spray drying methods in accordance with the invention are described in the Examples herein and in U.S. Pat. Nos. 6,848,197 and 8,197,845, incorporated herein by reference.

If desired, the respirable dry particles that are produced can be fractionated by volumetric size, for example, using a sieve, or fractioned by aerodynamic size, for example, using a cyclone, and/or further separated according to density using techniques known to those of skill in the art.

In some embodiments, the simvastatin or L-Car particles are generated by a method, comprising: a) preparing a first solution comprising said simvastatin in an organic solvent; and b) spraying the first solution using a spray drying apparatus. In some embodiments, the method further comprises the steps of preparing a second solution comprising said pharmaceutically acceptable carrier in an organic solvent; and co-spraying the first and second solutions. In some embodiments, the organic solvent is methanol.

Administration to the respiratory tract may also be achieved by means of an aerosol formulation in which the active ingredient is provided in a pressurized pack with a suitable propellant. If the compounds or pharmaceutical compositions comprising them are administered as aerosols, for example as nasal aerosols or by inhalation, this can be carried out, for example, using a spray, a nebulizer, a pump nebulizer, an inhalation apparatus, a metered inhaler or a dry powder inhaler. Pharmaceutical forms for administration of the compounds as an aerosol can be prepared by processes well known to the person skilled in the art. For their preparation, for example, solutions or dispersions of the compounds in water, water/alcohol mixtures or suitable saline solutions can be employed using customary additives, for example benzyl alcohol or other suitable preservatives, absorption enhancers for increasing the bioavailability, solubilizers, dispersants and others and, if appropriate, customary propellants, for example include carbon dioxide, CFCs, such as, dichlorodifluoromethane, trichlorofluoromethane, or dichlorotetrafluoroethane; and the like. The aerosol may conveniently also contain a surfactant such as lecithin. The dose of drug may be controlled by provision of a metered valve.

In formulations intended for administration to the respiratory tract, including intranasal formulations, the compound will generally have a small particle size for example of the order of 50 microns or less. Such a particle size may be obtained by means known in the art, for example by micronization. When desired, formulations adapted to give sustained release of the active ingredient may be employed.

Alternatively the active ingredients may be provided in the form of a dry powder, for example, a powder mix of the compound in a suitable powder base such as lactose, starch, starch derivatives such as hydroxypropylmethyl cellulose and polyvinylpyrrolidone (PVP).

The compounds may optionally exist as pharmaceutically acceptable salts including pharmaceutically acceptable acid addition salts prepared from pharmaceutically acceptable non-toxic acids including inorganic and organic acids. Representative acids include, but are not limited to, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. Certain pharmaceutically acceptable salts are listed in Berge, et al., Journal of Pharmaceutical Sciences, 66:1-19 (1977), incorporated herein by reference in its entirety.

Additional embodiments provide a system, comprising: the Sim and/or L-Car compositions described herein; and a dry powder inhaler device (e.g., commercially available devices). The inhaler may be a single dose or multi-dose inhaler.

In one aspect of this invention, an inhaler is a dry powder inhaler. A variety of inhalers can be used including the Aerolizer, Diskus, Flexhaler, Handihaler, Neohaler, Pressair, Rotahaler, Turbohaler, and Twisthaler. Other dry powder inhalers which can be used are described in U.S. Pat. Nos. 6,766,799, 7,278,425 and 8,496,002, each of which are hereby incorporated in by reference for their disclosure relating to the inhalation devices described therein. In one aspect of the invention, the compartment is a capsule or a blister pack. In one aspect of the invention, the inhaler has a resistance of about 0.05 to about 0.25, about 0.15 to about 0.25, 0.05 to about 0.15, 0.2 to about 0.25, or about 0.2. Resistance as referred herein is measured in: Square root of $CmH_2O$/Liters 20 per minute. Gravimetric analysis, using Cascade impactors, is a method of measuring the size distribution of airborne particles. Another method for measuring the size distribution of airborne particles is the Multi-stage liquid Impinger (MSLI). The MSLI is used to provide an indication of the flow rate dependence of the powder.

As used herein, the term "nominal powder dose" is the total amount of powder held in a capsule. As used herein, the term "nominal drug dose" is the total amount of Sim and/or L-Car contained in the nominal powder dose. The nominal powder dose is related to the nominal drug dose by the load percent of drug in the powder.

Tap density can be measured by using instruments known to those skilled in the art such as the Dual Platform Microprocessor Controlled Tap Density Tester (Vankel, N.C.) or a GEOPYC™ instrument (Micrometries Instrument Corp., Norcross, Ga., 30093). Tap density is a standard measure of the envelope mass density. Tap density can be determined using the method of USP Bulk Density and Tapped Density, United States Pharmacopia convention, Rockville, Md., 10th Supplement, 4950-4951, 1999. Features which can contribute to low tap density include irregular surface texture and porous structure. The envelope mass density of an isotropic particle is defined as the mass of the particle divided by the minimum sphere envelope volume within which it can be enclosed.

The diameter of the spray-dried particles, for example, the VMGD, can be measured using a laser diffraction instrument (for example Helos, manufactured by Sympatec, Princeton, N.J.). Other instruments for measuring particle diameter are well known in the art.

In some embodiments, the inhalable powder comprising Sim and/or L-Car as described above is used to fill capsules suitable for use in an inhaler. The term "capsule material" as used herein refers to the material from which the shell of the capsule for inhalation is made. In one embodiment, the capsule material according to the invention is selected from among gelatin, cellulose derivatives, starch, starch derivatives, chitosan and synthetic plastics. If gelatin is used as the capsule material, examples according to the invention may be selected from among polyethyleneglycol (PEG), PEG 3350, glycerol, sorbitol, propyleneglycol, PEO-PPO block copolymers and other polyalcohols and polyethers. If cellulose derivatives are used as the capsule material, examples according to the invention may be selected from hydroxypropylmethylcellulose (HPMC), hydroxypropylcellulose, methylcellulose, hydroxymethylcellulose and hydroxyethylcellulose. In one embodiment, the capsule size is selected from 000, 00, 0, 1, or 2.

In one aspect of the invention, the powders have low electrostatic charge to enable high dispersion from the capsule. The capsules of the invention are particularly suitable for use in a dry powder inhaler for the delivery of a dry powder composition comprising an effective amount of Sim and/or L-Car to a patient in need thereof for example, for treating pulmonary disease.

The present invention provided methods of administering Sim and/or L-Car to the lung for any use (e.g., treatment of diseases currently or not treated with Sim and/or L-Car such as PH, asthma, COPD, acute lung injury, radiation-induced lung injury or other disorders not currently treated by Sim and/or L-Car.

Further embodiments provide a method of treating (PH) in a subject, comprising: administering the Sim and/or L-Car compositions described herein to a subject diagnosed with or having signs or symptoms of PH under conditions such that the signs or symptoms are reduced. In some embodiments, the method further comprises administering an additional treatment for PH (e.g., including but not limited to, a vasodilator, an anticoagulant, an antiplatelet agent, an anti-inflammatory agent, or a vascular-remodeling therapy). In some embodiments, the composition s administered to the lung of the subject using a dry powder inhaler.

Still further embodiments provide the use of the Sim and/or L-Car compositions described herein to treat PH in a subject diagnosed with or having signs or symptoms of PH.

Yet other embodiments provide the Sim and/or L-Car compositions described herein for use in treating PH in a subject diagnosed with or having signs or symptoms of PH.

Also provided herein is a method of administering Sim and/or L-Car to the lung of a subject, comprising: delivering the Sim and/or L-Car compositions described herein to the lung of a subject using a dry powder inhaler.

EXPERIMENTAL

Example 1

Materials and Methods

Materials

Figure 1B:
Figure 1C:
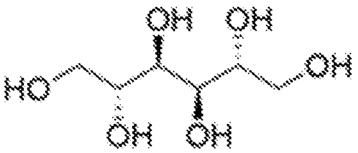

Sim [United Stated Pharmacopeia (USP) grade] [C25H3805; molecular weight (MW): 418.566 g/mol], raw Man, ACS reagent (C6H1406; MW: 182.17 g/mol) and raw L-Car, 99+% purity (C7H15NO3; MW: 161.199 g/mol) were obtained from ACROS (New Jersey, USA), shown in FIG. 1 (ChemDraw Ultra Ver. 15.0.; CambridgeSoft, Cambridge, Mass.). Methanol (HPLC grade, ACS-certified grade, purity 99.9%) was obtained from Fisher Scientific (Fair Lawn, N.J.). HYDRANAL®-Coulomat AD was from Sigma-Aldrich. Raw Sim and L-Car were stored in sealed glass desiccators over indicating Drierite/Drierite™ desiccant at −20° C. under ambient pressure. Man was stored under room conditions. Other chemicals were stored under room conditions. The nitrogen gas used was ultra-high purity (UHP) nitrogen gas (Cryogenics and gas facility, The University of Arizona, Tucson, Ariz.).

Human pulmonary cell lines from different regions of the lung were purchased from the American Type Culture Collection ATCC® A549 (ATCC® CCL185™) and H358 (ATCC® CRL-5807™). Dulbecco's modified Eagle's medium (DMEM), Advanced 1×, Fetal Bovine Serum (FBS), Pen-Strep, Fungizone®, and L-Glutamine were obtained from gibco® by Life Technologies (Thermo Fisher Scientific Inc, USA).

Methods

Preparation of SD and Co-SD Particles by Organic Solution Advanced Co-Spray Drying (No Water) in Closed Mode As previously reported (Li, X., et al., J Aerosol Med Pulm Drug Deliv, 2014. 27(2): p. 81-93; Li, X., et al., European Journal of Pharmaceutical Sciences, 2014. 52: p. 191-205; Meenach, S. A., et al., AAPS PharmSciTech, 2014. 15(6): p. 1574-87; Li, X., et al., Pharm Sci, 2014. 103(9): p. 2937-49; Meenach, S. A., et al., European Journal of Pharmaceutical Sciences, 2013. 49(4): p. 699-797; Muralidharan, P., et al., The Royal Society of Chemistry(RSC): Molecular Systems Design & Engineering, 2016: p. 1-18) using different conditions, organic solution advanced spray drying and co-spray drying processing in the absence of water was performed in close-mode using a Büchi B-290 Mini Spray Dryer with a high performance cyclone in close mode using UHP dry nitrogen gas as the atomizing gas and connected to the B-295 Inert Loop (Büchi Labortechnik A G, Flawil, Switzerland). The feed solutions were prepared by dissolving the components in methanol using Branson 7500 ultrasonicator to assistance in dissolution. Different feed solutions were prepared: Sim and L-Car, separately, were dissolved in methanol to make dilute solutions with a final concentration of 0.5% (w/v), each one. The feed solutions of the two components formulations consisting of Sim with Man and of Sim with L-Car with rationally selected molar ratios were prepared by dissolving each component in methanol to make a total powder concentration of 0.2% (w/v) and 0.5% (w/v), respectively. Table 1 lists the spray drying conditions for one and two component powders.

The drying gas atomization rate (670 L/h at 35 mmHg), the aspiration rate (35 m3/h at 100% rate) and the inlet temperature (150° C.) were maintained constant during all the experiments. The corresponding outlet temperatures are summarized in Table 2. The stainless steel nozzle diameter was 0.7 mm The Co-SD particles were separated from the nitrogen drying gas in the high-performance cyclone and collected in the small sample collector. All Co-SD powders were carefully stored in sealed glass vials stored in sealed glass desiccators over Indicating Drierite/Drierite™ desiccant at −20° C.

Scanning Electron Microscopy

Using conditions similar to previously reported (Li, X., et al., J Aerosol Med Pulm Drug Deliv, 2014. 27(2): p. 81-93; Li, X., et al., European Journal of Pharmaceutical Sciences, 2014. 52: p. 191-205; Meenach, S. A., et al., AAPS PharmSciTech, 2014. 15(6): p. 1574-87; Li, X., et al., Pharm Sci, 2014. 103(9): p. 2937-49; Meenach, S. A., et al., European Journal of Pharmaceutical Sciences, 2013. 49(4): p. 699-797; Muralidharan, P., et al., The Royal Society of Chemistry(RSC): Molecular Systems Design & Engineering, 2016: p. 1-18), visual imaging and analysis of particle size, morphology, and surface morphology were achieved by scanning electron microscopy (SEM) using a FEI Inspect S microscope (FBI, Brno, Czech republic).

Samples were placed on double-sided adhesive carbon tabs (TedPella, Inc. Redding Calif.), which were adhered to aluminum stubs (TedPella, Inc.) and were coated with a gold thin film using a Hummer 6.2 sputtering system from Anatech (Union City, Calif.). The coating process was operated at 15 AC milliAmperes with about 7 kV of voltage for 3 minutes. The electron beam with an accelerating voltage of 30 kV was used at a working distance of 9-12.5 mm. Several magnification levels were used.

Particle Sizing and Size Distribution Using SEM Micrographs

The mean size, standard deviation, and size range were determined using SigmaScan™ Pro 5.0.0 (Systat, Inc., San Jose, Calif.) based on their scanning electron micrographs using a similar procedure that we have previously reported (Muralidharan et al., supra; Meenach, S. A., et al., AAPS PharmSciTech, 2014. 15(6): p. 1574-87). Representative micrographs for each particle sample at 3000× magnification was analyzed by measuring the diameter of at least 100 particles per sample.

X-Ray Powder Diffraction

Using conditions similar to previously reported (Li, X., et al., J Aerosol Med Pulm Drug Deliv, 2014. 27(2): p. 81-93; Li, X., et al., European Journal of Pharmaceutical Sciences, 2014. 52: p. 191-205; Meenach, S. A., et al., AAPS PharmSciTech, 2014. 15(6): p. 1574-87; Li, X., et al., Pharm Sci, 2014. 103(9): p. 2937-49; Meenach, S. A., et al., European Journal of Pharmaceutical Sciences, 2013. 49(4): p. 699-797; Muralidharan, P., et al., The Royal Society of Chemistry(RSC): Molecular Systems Design & Engineering, 2016: p. 1-18), the degree of long range molecular order (crystallinity) for all powders was measured by X-ray powder diffraction (XRPD). XRPD patterns of samples were collected at room temperature with a PANalytical X'pert diffractometer (PANalytical Inc., Westborough, Mass., USA) equipped with a programmable incident beam slit and an X'Celerator Detector. The x-ray radiation used was Ni-filtered Cu Kα (45 kV, 40 Ma, and $\lambda$=1.5418 Å). 264 Measurements were made between 5.0° and 60.0° (2θ) with a scan rate of 2°/min. The powder samples were loaded on zero background silicon wafer sample holder Differential Scanning Calorimetry Using conditions similar to previously reported (Li, X., et al., J Aerosol Med Pulm Drug Deliv, 2014. 27(2): p. 81-93; Li, X., et al., European Journal of Pharmaceutical Sciences, 2014. 52: p. 191-205; Meenach, S. A., et al., AAPS PharmSciTech, 2014. 15(6): p. 1574-87; Li, X., et al., Pharm Sci, 2014. 103(9): p. 2937-49; Meenach, S. A., et al., European Journal of Pharmaceutical Sciences, 2013. 49(4): p. 699-797; Muralidharan, P., et al., The Royal Society of Chemistry(RSC): Molecular Systems Design & Engineering, 2016: p. 1-18), thermal analysis and phase transition measurements were performed on a TA Q1000 differential scanning calorimetry (DSC) (TA Instruments, New Castle, Del.) equipped with T-Zero® technology, RSC90 automated cooling system, auto sampler and calibrated with indium. Approximately 1-10 mg sample was placed into an anodized aluminum hermetic DSC pan. The T-Zero® DSC pans were hermetically sealed with the T-Zero hermetic press (TA Instruments). An empty hermetically sealed aluminum pan was used as reference pan for all the experiments. UHP nitrogen was used as the purging gas at a rate of 40 mL/min The samples were heated from at least 0.00° C. to 200.00° C. at a scanning rate of 5.00° C./min. All measurements were carried out in triplicate (n=3).

Hot Stage Microscopy (HSM) Under Cross-Polarizers

Using conditions similar to previously reported (Li, X., et al., J Aerosol Med Pulm Drug Deliv, 2014. 27(2): p. 81-93; Li, X., et al., European Journal of Pharmaceutical Sciences, 2014. 52: p. 191-205; Meenach, S. A., et al., AAPS PharmSciTech, 2014. 15(6): p. 1574-87; Li, X., et al., Pharm Sci, 2014. 103(9): p. 2937-49; Meenach, S. A., et al., European Journal of Pharmaceutical Sciences, 2013. 49(4): p. 699-797; Muralidharan, P., et al., The Royal Society of Chemistry(RSC): Molecular Systems Design & Engineering, 2016: p. 1-18), hot-stage microscopy (HSM) were performed using a Leica DMLP cross-polarized microscope (Wetzlar, Germany) equipped with a Mettler FP 80 central processor heating unit and Mettler FP82 hot stage (Columbus, Ohio, USA). Samples were mounted on a glass slide and heated from at least 25.0° C. to 200.0° C. at a heating rate of 5.00° C./min. The images were digitally captured using a Nikon coolpix 8800 digital camera (Nikon, Tokyo, Japan) under 10× optical objective and 10× digital zoom.

Karl Fisher Titration (KFT)

Using conditions similar to previously reported (Li, X., et al., J Aerosol Med Pulm Drug Deliv, 2014. 27(2): p. 81-93; Li, X., et al., European Journal of Pharmaceutical Sciences, 2014. 52: p. 191-205; Meenach, S. A., et al., AAPS PharmSciTech, 2014. 15(6): p. 1574-87; Li, X., et al., Pharm Sci, 2014. 103(9): p. 2937-49; Meenach, S. A., et al., European Journal of Pharmaceutical Sciences, 2013. 49(4): p. 699-797; Muralidharan, P., et al., The Royal Society of Chemistry(RSC): Molecular Systems Design & Engineering, 2016: p. 1-18), the residual water content of all SD and Co-SD powders were quantified analytically by Karl Fischer titration (KFT) coulometrically using a TitroLine 7500 trace titrator (SI Analytics, Germany).

Approximately 2-10 mg of powder was added to the titration cell containing Hydranal® Coulomat AD reagent. The residual water content was then calculated.

Raman Spectroscopy

Raman spectroscopy provides noninvasive and nondestructive microspectroscopic component analysis of DPI formulations. Using similar conditions previously reported (Li, X., et al., J Aerosol Med Pulm Drug Deliv, 2014. 27(2): p. 81-93; Li, X., et al., European Journal of Pharmaceutical Sciences, 2014. 52: p. 191-205; Meenach, S. A., et al., AAPS PharmSciTech, 2014. 15(6): p. 1574-87; Li, X., et al., Pharm Sci, 2014. 103(9): p. 2937-49; Meenach, S. A., et al., European Journal of Pharmaceutical Sciences, 2013. 49(4): p. 699-797; Muralidharan, P., et al., The Royal Society of Chemistry(RSC): Molecular Systems Design & Engineering, 2016: p. 1-18), Raman spectra was obtained at 514 nm laser excitation using Renishaw InVia Reflex (Gloucestershire, UK) at the surface using a 20× magnification objective on a Leica DM2700 optical microscope (Wetzlar, Germany) and equipped with a Renishaw inVia Raman system (Gloucestershire, UK). This Renishaw system has a 2400 l/mm grating, with a slit width of 65 μm and a thermoelectrically cooled Master Renishaw CCD detector. The laser power was adjusted to achieve 5000 counts per second for the 520 cm-1 line of the internal Si Reference. Raman spectra was performed using 1% of laser power, and 10 seconds of exposure in all samples.

Attenuated Total Reflectance—FTIR Spectroscopy

A Nicolet Avatar 360 FTIR spectrometer (Varian Inc., CA) equipped with a DTGS detector and a Harrick MNP-Pro (Pleasantville, N.Y., USA) attenuated total reflectance (ATR) accessory was used for all the experiments. Each spectrum was collected for 32 scans at a spectral resolution of 2 cm-1 over the wavenumber range of 4000-400 cm-1. A background spectrum was carried out under the same experimental 308 conditions and was subtracted from each sample spectrum. Spectral data were acquired with EZ-OMNIC software. These conditions are similar to previous reports (Li, X., et al., J Aerosol Med Pulm Drug Deliv, 2014. 27(2): p. 81-93; Li, X., et al., European Journal of Pharmaceutical Sciences, 2014. 52: p. 191-205; Meenach, S. A., et al., AAPS PharmSciTech, 2014. 15(6): p. 1574-87; Li, X., et al., Pharm Sci, 2014. 103(9): p. 2937-49; Meenach, S. A., et al., European Journal of Pharmaceutical Sciences, 2013. 49(4): p. 699-797; Muralidharan, P., et al., The Royal Society of Chemistry(RSC): Molecular Systems Design & Engineering, 2016: p. 1-18).

In Vitro Aerosol Dispersion Performance

In accordance with USP Chapter<601> specifications on aerosols and using conditions similar to previously reported (Li, X., et al., J Aerosol Med Pulm Drug Deliv, 2014. 27(2): p. 81-93; Li, X., et al., European Journal of Pharmaceutical Sciences, 2014. 52: p. 191-205; Meenach, S. A., et al., AAPS PharmSciTech, 2014. 15(6): p. 1574-87; Li, X., et al., Pharm Sci, 2014. 103(9): p. 2937-49; Meenach, S. A., et al., European Journal of Pharmaceutical Sciences, 2013. 49(4): p. 699-797; Muralidharan, P., et al., The Royal Society of Chemistry(RSC): Molecular Systems Design & Engineering, 2016: p. 1-18), the aerosol dispersion performance of SD Sim, L-Car and Co-SD particles was tested using the Next Generation Impactor™ (NGI™) (MSP Corporation, Shoreview, Minn., USA) with a stainless steel induction port (USP throat) attachment (NGI Model 170; MSP Corporation) equipped with specialized stainless steel NGI gravimetric insert cups (MSP Corporation) and FDA approved human DPI device HandiHaler® (Boehringer Ingelheim, Ingelheim, Germany). An airflow rate (Q) of 60 L/min (adult airflow rate) was adjusted and measured before each experiment using a COPLEY DFM 2000 flow meter (COPLEY Scientific, Nottingham, United Kingdom). The NGI was connected to a COPLEY HCPS vacuum pump (COPLEY Scientific) through a COPLEY TPK 2000 critical flow controller (COPLEY Scientific). The mass of powder deposited on each stage was quantified by gravimetric method using type A/E glass fiber filters with diameter 55 mm (PALL Corporation, Port Washington, N.Y.) and 75 mm (Advantec, Japan). Quali-V clear HPMC size 3 inhalation grade capsules (Qualicaps, North Carolina) were filled with about 10 mg of powder was used. Three capsules were used in each experiment. In vitro aerosolization was evaluated in triplicate (n=3) under ambient conditions.

For the NGI, Q=60 L/min, the Da50 aerodynamic cutoff diameter 329 for each NGI stage was calibrated by the manufacturer and stated as: stage 1 (8.06 μm); stage 2 (4.46 μm); stage 3 (2.82 μm); stage 4 (1.66 μm); stage 5 (0.94 μm); stage 6 (0.55 μm); and stage 7 (0.34 μm). The emitted dose (ED) was determined as the difference between the initial mass of powder loaded in the capsules and the remaining mass of powder in the capsules following the aerosolization. The ED (%) Equation 1 was used to express the percentage of ED based on the total dose (TD) used. The fine particle dose (FPD) was defined as the dose deposited on stages 2 to 7. The fine particle fraction (FPF %) Equation 2 was expressed as the percentage of FPD to ED. The respirable fraction (RF %) Equation 3 was used as the percentage of FPD to total deposited dose (DD) on all impactor stages.

$$\text{Emitted Dose fraction } (ED\ \%) = \frac{ED}{TD} \times 100\% \quad \text{Equation 1}$$

$$\text{Fine Particle Fraction } (FPF\ \%) = \frac{FPD}{ED} \times 100\% \quad \text{Equation 2}$$

$$\text{Respirable Fraction } (RF\ \%) = \frac{FPD}{DD} \times 100\% \quad \text{Equation 3}$$

In addition, the mass median aerodynamic diameter (MMAD) of aerosol particles and geometric standard deviation (GSD) were calculated using a Mathematica (Wolfram Research, Inc., Champaign, Ill.) program written by Dr. Warren Finlay.

In Vitro Cell Dose Response Assay

The effects of SD and Co-SD formulations on cell proliferation were analyzed by measuring the response of lung adenocarcinoma and bronchoalveolar carcinoma cells (A549 and H358, respectively) to different concentrations. The A549 pulmonary cell line is a human alveolar epithelial lung adenocarcinoma cell line and is also used as a model of the alveolar type II pneumocyte cell in in vitro pulmonary drug delivery 350 and metabolism studies (Haghi, M., et al., Pharmacol Ther, 815 2014. 144(3): p. 235-52). The H358 pulmonary cell line is a human bronchoalveolar epithelial cell line similar to alveolar type II cells and express lung surfactant associated protein A (SP-A) (Haghi et al., supra). Cell lines were grown in a growth medium including Dulbecco's modified Eagle's medium (DMEM), Advanced 1×, 10% (v/v) fetal bovine serum (FBS), Pen-Strep (100 U ml-1 penicillin, 100 μg ml-1), Fungizone (0.5 μg ml-1 amphotericin B, 0.41 μg ml-1 sodium deoxycholate), and 2 mM L-Glutamine in a humidified incubator at 37° C. and 5% $CO_2$, as previously reported (Meenach, S. A., et al., AAPS PharmSciTech, 739 2014. 15(6): p. 1574-87).

A549 and H358 cells were seeded in 96-well plates at 5000 cells/well and 100 μl/well and were allowed 48 hours to attach. The cells were then exposed to different concentrations of the SD and Co-SD formulations, as previously reported (Meenach, S. A., et al., AAPS PharmSciTech, 739 2014. 15(6): p. 1574-87). The drug solution was prepared by dissolving the drug particles in 3% DMSO and 97% DMEM media. One hundred microliters (μl) of this drug solution or control solution (3% DMSO and 97% DMEM media) was added to each well. Seventy-two (72) hours after exposure, 20 μl of 20 μM resazurin sodium salt was added to each well and incubated for 4 hours. At this point, the fluorescence intensity of the resorufin (metabolite) produced by viable cells was detected at 544 nm (excitation) and 590 nm (emission) using the Synergy H1 Multi-Mode Reader (BioTek Instruments, Inc., Winooski, Vt.). The relative viability of cell line was calculated as follow by equation 4:

Relative viability (%)=Sample fluorescence intensity Control fluorescence intensity 369×100% (4)

In Vitro Transepithelial Electrical Resistance (TEER) Analysis upon Particle Exposure to Lung Epithelial Cells Calu-3 lung epithelial cells, a human lung adenocarcinoma cell line derived from the bronchial submucosal airway region, were grown in a growth medium including Eagle's minimum essential medium (EMEM), 10% (v/v) fetal bovine serum (FBS), Pen-Strep (100 U ml-1 penicillin, 100 μg ml-1), Fungizone (0.5 μg ml-1 amphotericin B, 0.41 μg ml-1 sodium deoxycholate) in humidified incubator at 37° C. and 5% CO2, as previously reported (Meenach, S. A., et al., AAPS PharmSciTech, 739 2014. 15(6): p. 1574-87; Meenach, S. A., et al., European Journal of Pharmaceutical Sciences, 2013. 49(4): p. 699-711). The cells were seeded at 500,000 cells/ml in Costar Transwells® (0.4 μm polyester membrane, 12 mm for a 12-well plate) with 0.5 ml of media on the apical side and 1.5 ml of media on the basolateral side. Media was changed every other day from the basolateral and apical side. After 5 days of growth, when the cells reached a TEER value of about 1000 Ω/cm2 (indicator of a confluent monolayer at liquid covered culture (LCC)) the media was removed from both sides and 500 μl of media was added to the basolateral side of the Transwells to facilitate air-interface culture (AIC) conditions. The TEER responses of the cells were measured with an Endohom 12 mm Culture Cup (World Precision Instruments, Sarasota, FL). For TEER measurement, 0.5 ml of media was added to the apical side of the Transwell 5 min before measurement and then immediately removed to return the cells to AIC conditions. After the TEER values reached 500 Ωcm2 (indicating a confluent monolayer at AIC conditions), the cells were exposed to 100 μM of representative SD and Co-SD formulations dissolved in 97% of EMEM media and 3% of DMSO, to facilitate dissolution. The liquid aerosol formulations were delivered to the Calu-3 cells at AIC by using a Penn Century MicroSprayer® Aerolizer-Model IA-1B. TEER values were then recorded after exposure up to 7 days after particle treatment, as previously reported (Meenach, S. A., et al., AAPS PharmSciTech, 739 2014. 15(6): p. 1574-87).

Statistical Analysis

All experiments were performed in at least triplicate (n=3). The results were analyzed statistically using Microsoft Office Excel 2007 (Microsoft Corporation, Redmond, Wash.). The results are expressed as the mean±standard deviation. All results were plotted using Sigma Plot 13.0 (Systat Software, Inc, San Jose, Calif.). T-test were carried by using also Sigma Plot 13.0 (Systat Software, Inc, San Jose, Calif.).

Results

Scanning Electron Microscopy (SEM)

Figure 2:
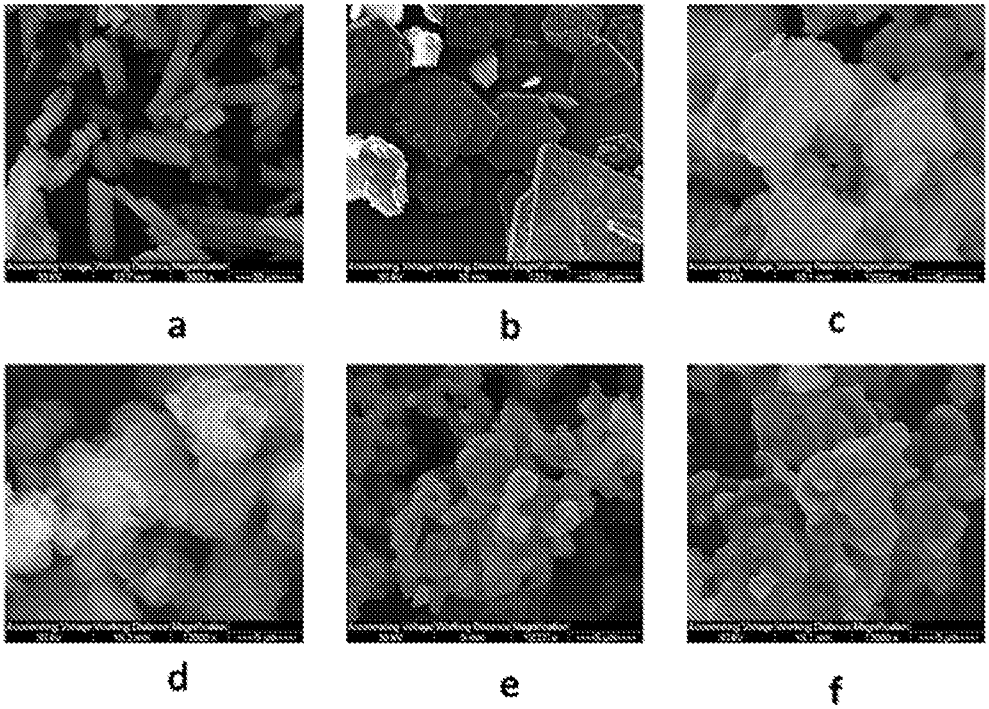
Figure 3:
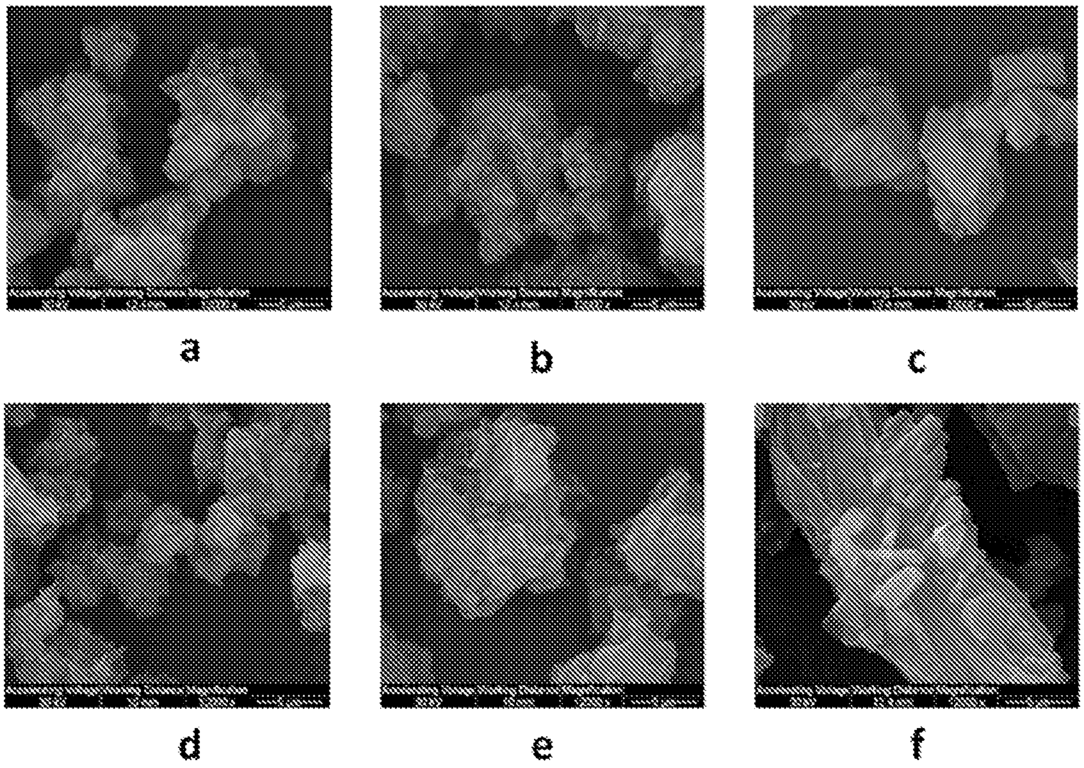
FIG. 3. SEM micrographs of Co-SD particles (magnification 12,000×): (a) Co-SD 50:50 Sim:man (25% PR); (b) Co-SD 70:30 Sim:man (25% PR); (C) Co-SD 70:30 Sim:man (50% PR); (d) Co-SD 90:10 Sim:man (25% PR); (e) Co-SD 90:10 Sim:man (50% PR); (f) Co-SD 90:10 Sim:L-Car (25% PR).

Size and morphology of Raw, SD and Co-SD particles were visualized by SEM and their micrographs are shown in FIGS. 2 and 3, respectively. Spray dried Sim was successfully produced at 25 and 50% pump rate. Both powders showed slightly wrinkled surface and equivalent sphere shape. Co-SD systems of Sim with Man also showed the same surface characteristic. The particles exhibited slightly sintering and agglomeration, although particle formation as equivalent spheres was achieved in almost all the ratios at 25% and 50% pump rates with the exception of Co-SD 50:50 Sim:Man that only was formed at 25% pump rate. SD L-Car was achieved at 25% and 50%. Sintering, agglomeration, and poor particle formation was observed in SEM micrographs. Corrugated and rough surfaces were also observed in these systems. Co-SD system of Sim with L-Car was only successfully attained at 90:10 ratio at 25% pump rate. This system showed large agglomerates consisting of particles with wrinkled topography interspersed with elongated particles.

Particle Sizing and Size Distribution by Image Analysis of SEM Micrographs

As shown in table 3, SD powders of Sim (25% and 50% PR) have a broad distribution but the mean of the particle size are about 10 and 7.8 microns, respectively. Co-SD systems are also showing a broad distribution but the mean of the particle size is about 9 microns. This is in agreement with SEM micrographs. The large distributions obtained were due to the difficulty to analyze the particle sizes of the different systems due to the aggregates that they were forming.

X-Ray Powder Diffraction (XRPD)

Figure 4:
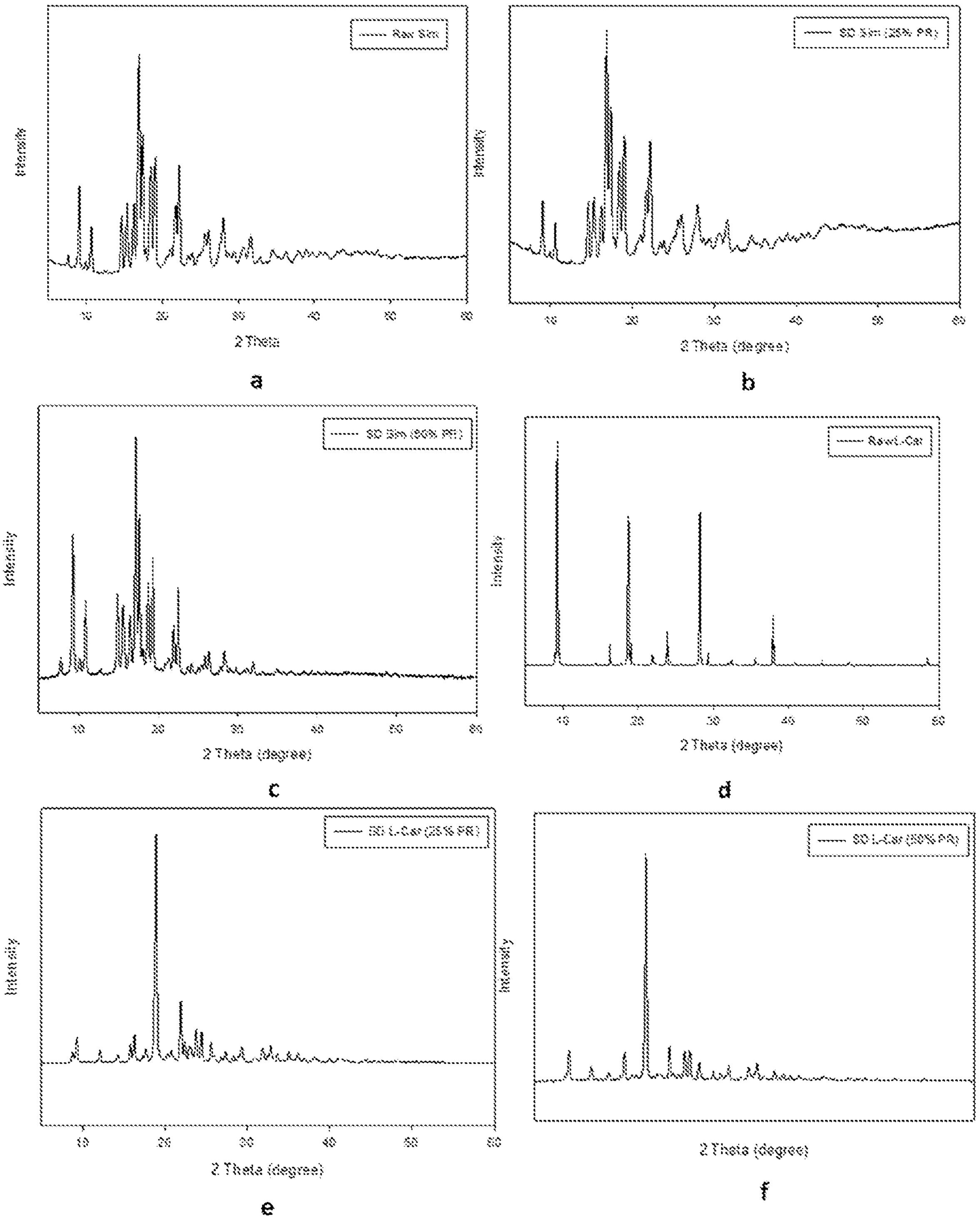
FIG. 4. XRPD Diffratograms for Raw, SD and Co-SD powders of: (a) Raw Sim; (b) SD Sim (25% PR); (c) SD Sim (50% PR) (d) Raw L-Car (e) SD L-Car (25% P); (f) SD L-Car (25% P); (g) Co-SD 90:10 Sim:L-Car (25% PR)
Figure 4:
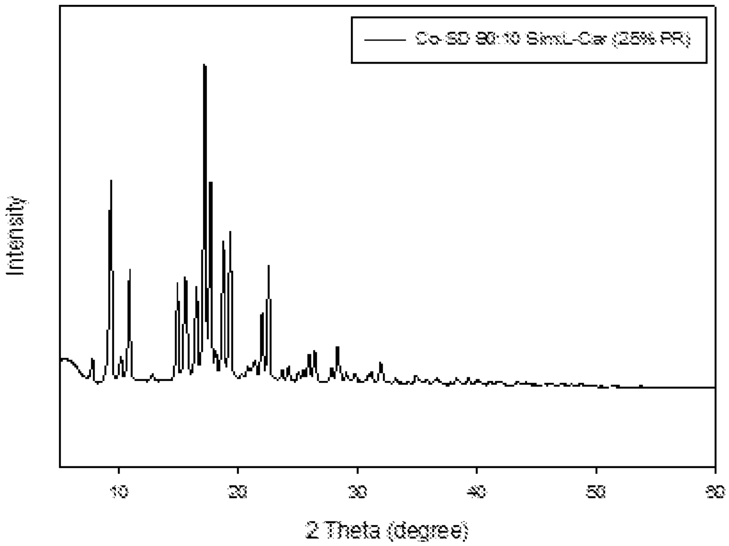

The XRPD pattern of raw Sim showed sharp and intense peaks (i.e long-range molecular order) due to the crystallinity of the drug. Numerous distinctive peaks at a diffraction angle of 2θ (9.10, 16.92, 17.38, 18.47, 19.06, and 22.21), as shown in FIG. 4, similarly with what it has been previously reported (Bolourchian, N., et al., Iranian Journal of Pharmaceutical Research: IJPR, 2013. 12(Suppl): p. 11-20; Jun, S. W., et al., Journal of Pharmaceutics and Biopharmaceutics, 2007. 66(3): p. 413-421; Rao, M., et al., Dissolution Technologies, 2010. 17(2): p. 27-34). SD Sim had the same pattern as raw Sim. XRPD pattern of L-Car also showed sharp and intense peaks due to the long-range molecular order of this compound. Distinctive peaks at a diffraction angle of 2θ (9.2, 16.2, 18.7, 23.9, 28.2 37.9) are in good agreement with what the literature shows. SD L-Car maintained the same diffraction pattern as the raw. XRPD of Raw Man and SD Man has been previously reported (Li, X., et al., J Aerosol Med Pulm Drug Deliv, 2014. 27(2): p. 731 81-93). Comparing with this previous report, the raw Man used in this study was found to be the beta form with peaks at 14.35, 18.50, 20.78, and 23.09.

Figure 5:
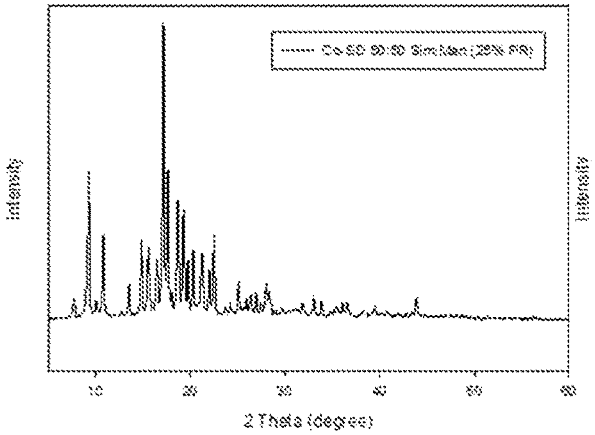
FIG. 5. XRPD Diffratograms for Co-SD powders of Sim and Man: (a) Co-SD 50:50 Sim:Man (25% PR); (b) Co-SD 70:30 Sim:Man (25% PR); (c) Co-SD 70:30 Sim:Man (50% PR); (d) Co-SD 90:10 Sim:Man (25% PR); (e) Co-SD 90:10 Sim:Man (50% PR)
Figure 5:
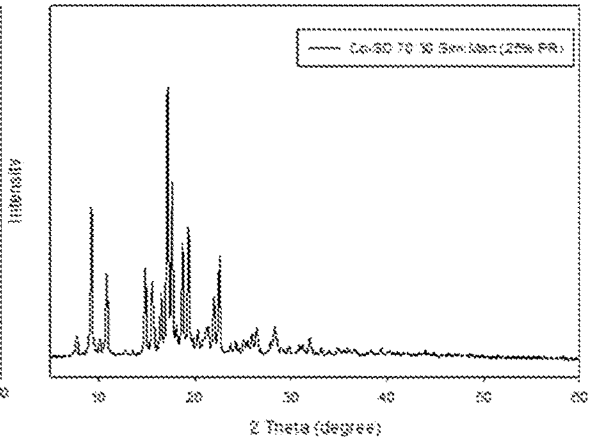
Figure 5:
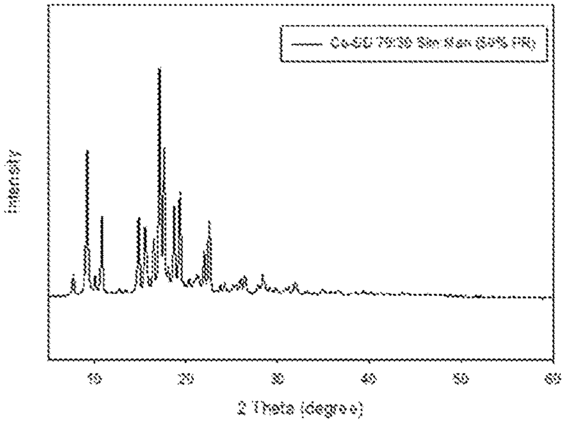
Figure 5:
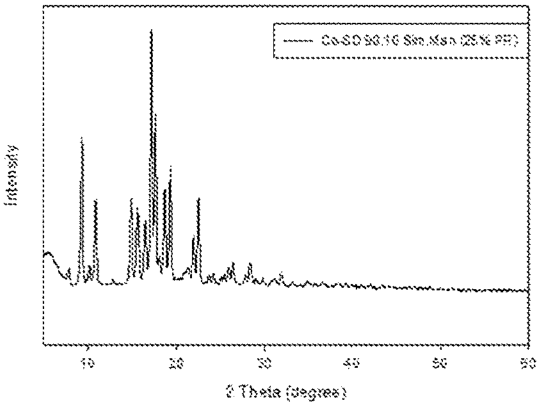
Figure 5:
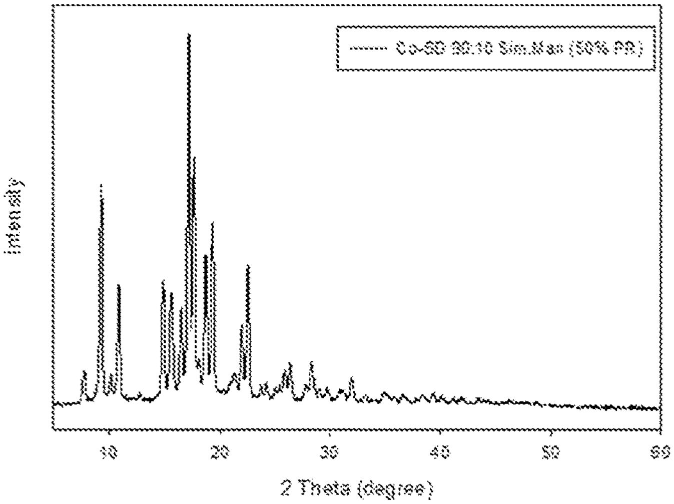

Co-SD systems patterns also reflected crystallinity. Sharp peaks in all Co-SD samples can be seen in FIGS. 4 and 5. All molar ratios and pump rates of Co-SD Sim with Man show similar diffraction patterns between them. All samples present slightly more similarity patterns to Raw Sim than to Raw Man, except Co-SD 50:50 Sim:Man that has many shared peaks with Raw Man. The molar ratio had no apparent effect 440 on the XRPD data for co-SD Sim:Man system. Retention of crystallinity by Man following spray drying was recently reported Li et al. [4] Co-SD Sim with L-Car has a similar pattern than Raw Sim. However, some peaks are matching also with Raw L-Car pattern.

Differential Scanning Calorimetry (DSC)

Figure 6:
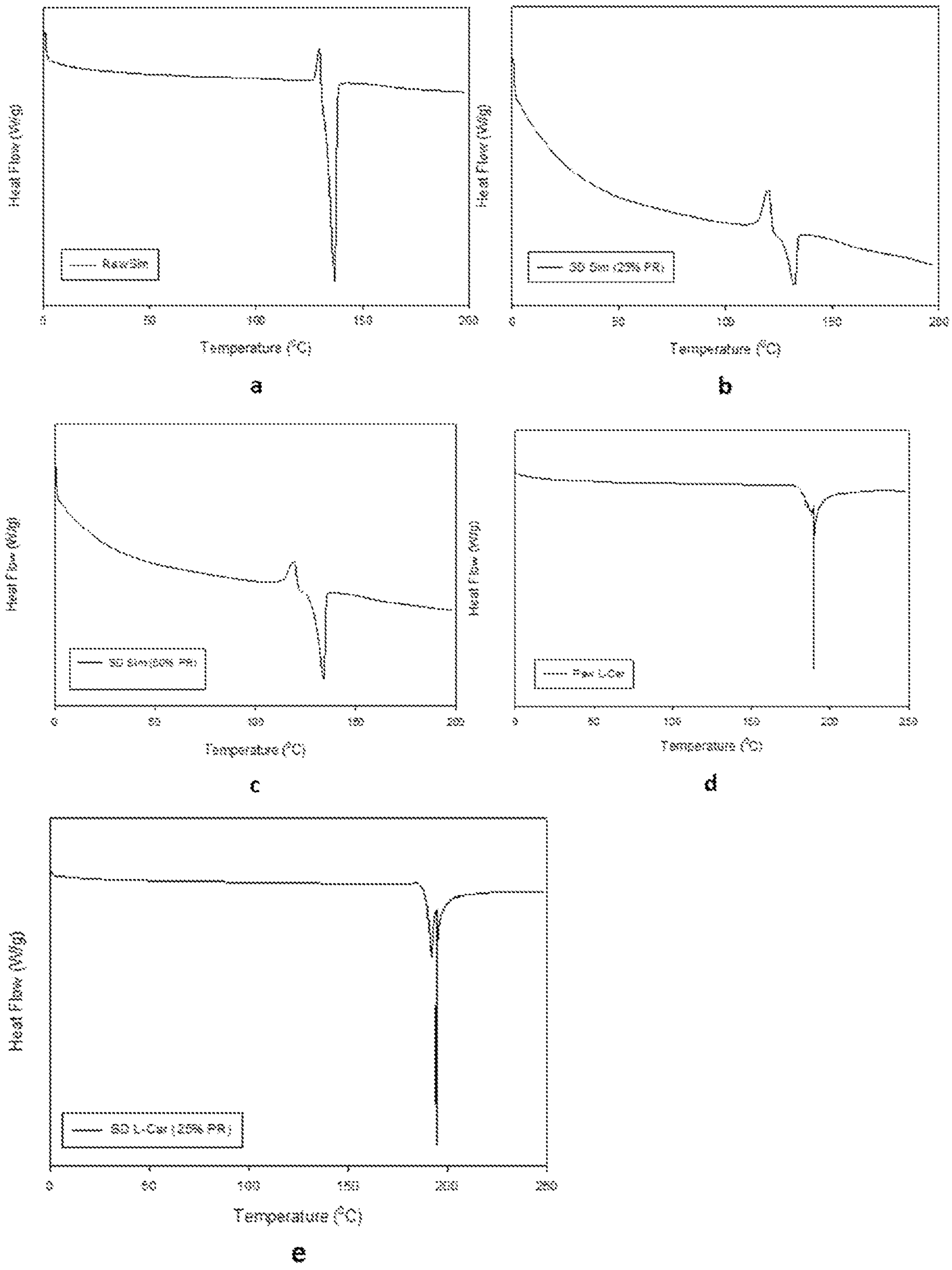
FIG. 6. DSC thermograms for Raw, SD and Co-SD powders of: (a) Raw Sim; (b) SD Sim (25% PR); (c) SD Sim (50% PR) (d) Raw L-Car (e) SD L-Car (25% P); (f) SD L-Car (25% P); (g) Co-SD 90:10 Sim:L-Car (25% PR)
Figure 6:
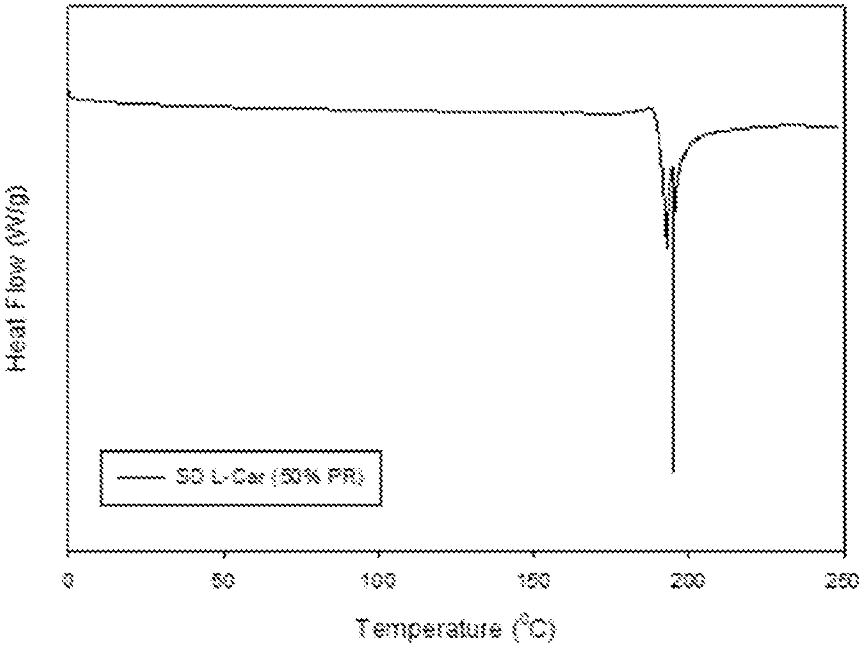
Figure 6:
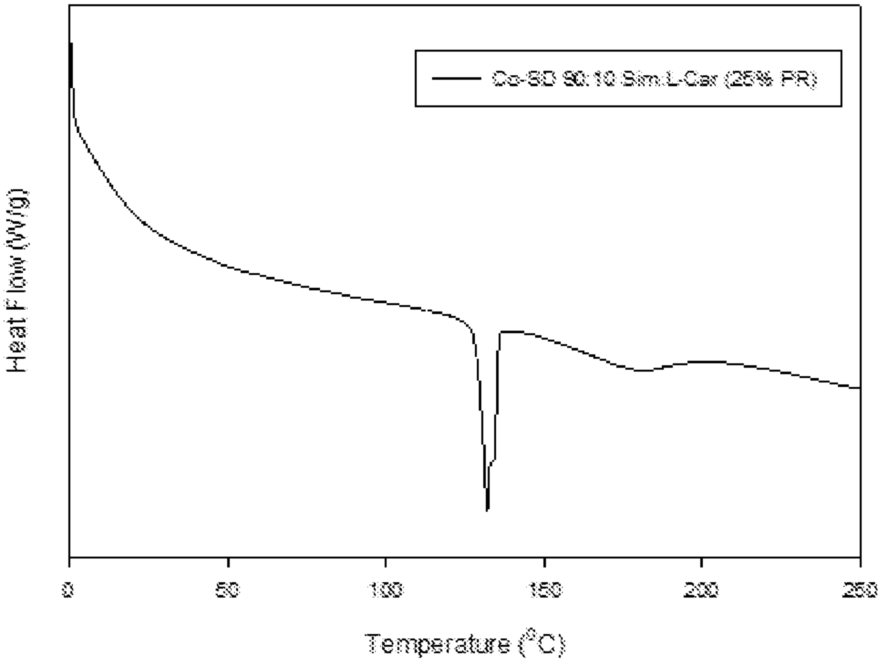
Figure 7:
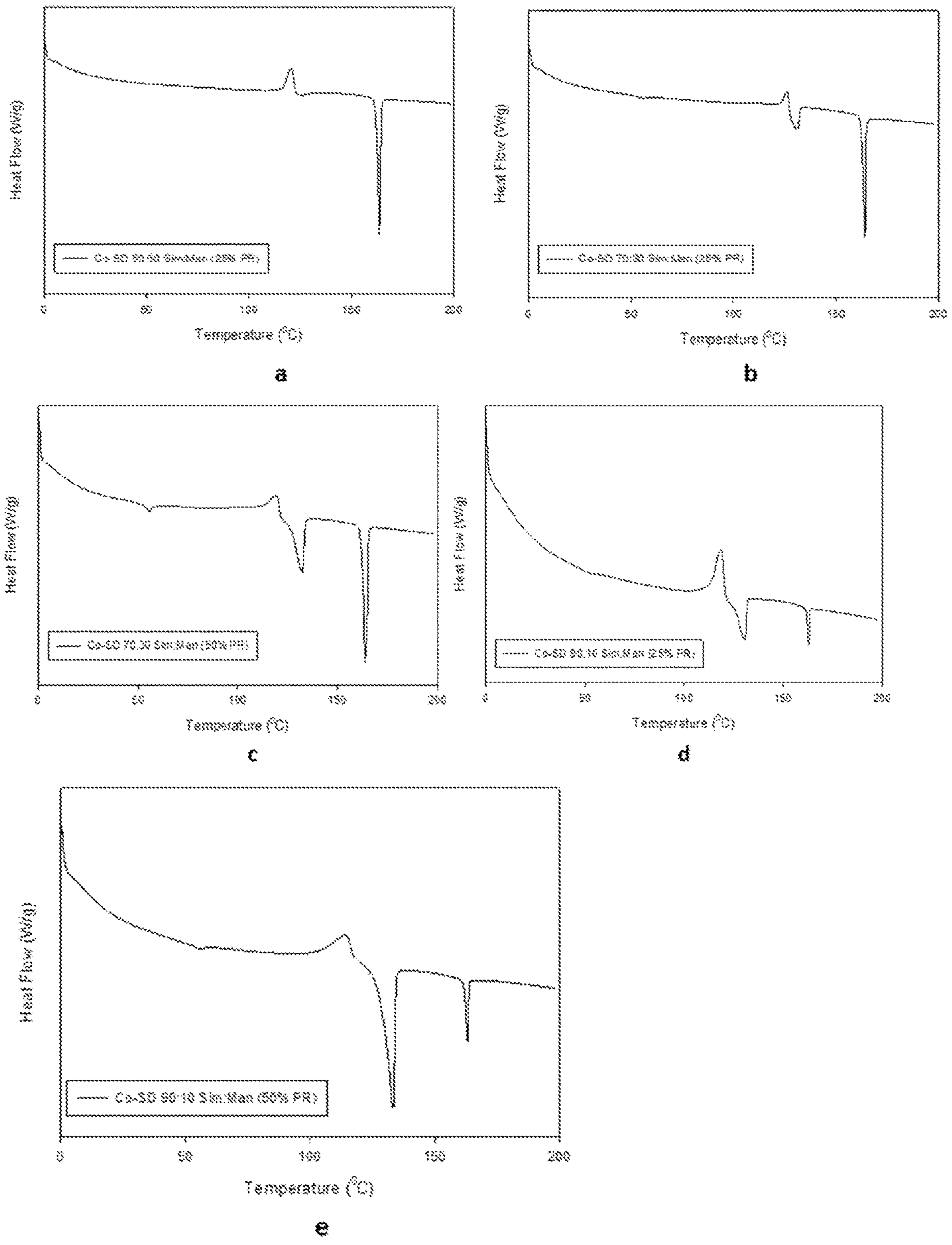
FIG. 7. DSC thermograms for Co-SD powders of Sim and Man: (a) Co-SD 50:50 Sim:Man (25% PR); (b) Co-SD 70:30 Sim:Man (25% PR); (c) Co-SD 70:30 Sim:Man (50% PR); (d) Co-SD 90:10 Sim:Man (25% PR); (e) Co-SD 90:10 Sim:Man (50% PR)

The thermograms of the raw, SD, and Co-SD particles are shown in FIGS. 6 and 7. Raw and SD (25 and 50% PR) Sim thermograms, show one small exotherm before the major endotherm at about 120° C. The major endotherm is observed at about 130° C. Fast DSC heating scans were conducted at 20° C./min and 40° C./min on all raw and SD Sim powders and no Tg was detected. Raw L-Car and SD L-Car (25 and 50% PR) thermograms show a single endothermic transition at about 190° C. Thermograms of all Co-SD systems of Sim with Man show one small exotherm and two major endotherms at about 120° C., 130° C., and 163° C., respectively. Fast DSC heating scans were conducted at 20° C./min and 40° C./min on all Co-SD systems of Sim with Man to discard the presence of Tg. Tg was not detected. In Co-SD Sim with L-Car thermogram, only one major endothermic transition is observed at about 130° C., indicating a possible encapsulation of Sim in L-Car. Phase transition temperatures and enthalpies for all systems are summarized in table 3.

Karl Fisher Titration (KFT)

The residual water content of all raw, SD, and Co-SD powders was quantified analytically by KFT. Residual water contents are shown in table 4. As expected, the addition of non hygroscopic Man to the Co-SD systems of Sim with Man decrease the amount of residual water content in comparison with the raw and the SD Sim. Co-SD Sim with L-Car shows more residual water content as expected due to the hygroscopicity of the L-Car. All these values are acceptable for dry powder inhalation aerosol formulations.

HSM Under Cross-Polarizer Lens

Figure 8:
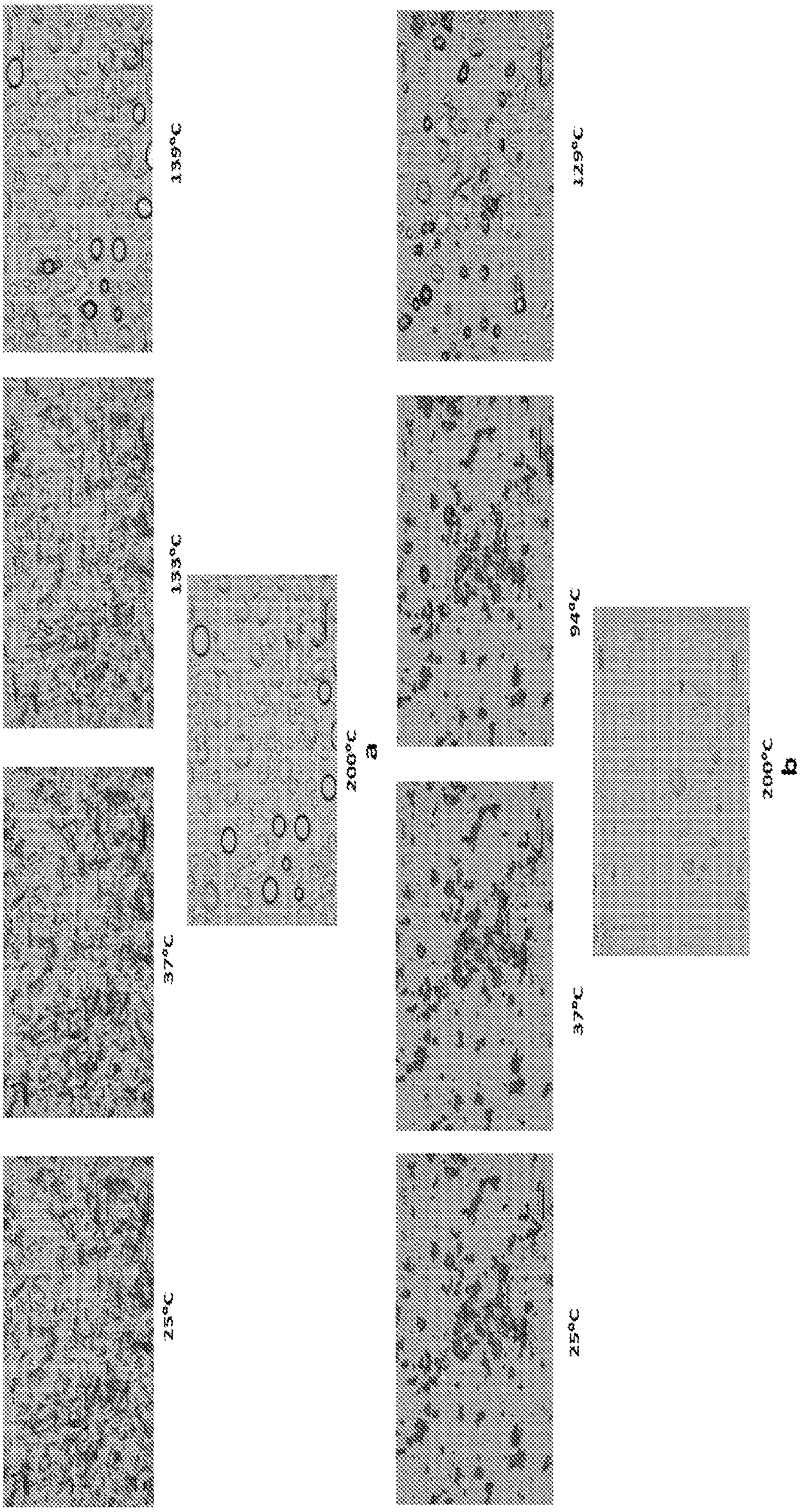
FIG. 8. Representative HSM micrographs of: (a) Raw Sim; (b) SD Sim (25% PR); (c) Raw L-Car; (d) SD L-Car (50% PR). Scale bar=10 μm FIG. 9. Representative HSM micrographs of: (a) Co-SD 50:50 Sim:Man (25% PR); (b) Co-SD 90:10 Sim:L-Car (25% PR). Scale bar=10 μm FIG. 10. ATR-FTIR spectra for Raw, SD and Co-SD powders of: (a) Raw Sim; (b) SD Sim (25% PR); (c) SD Sim (50% PR) (d) Raw L-Car (e) SD L-Car (25% P); (f) SD L-Car (25% P); (g) Co-SD 90:10 Sim:L-Car (25% PR)
Figure 8:
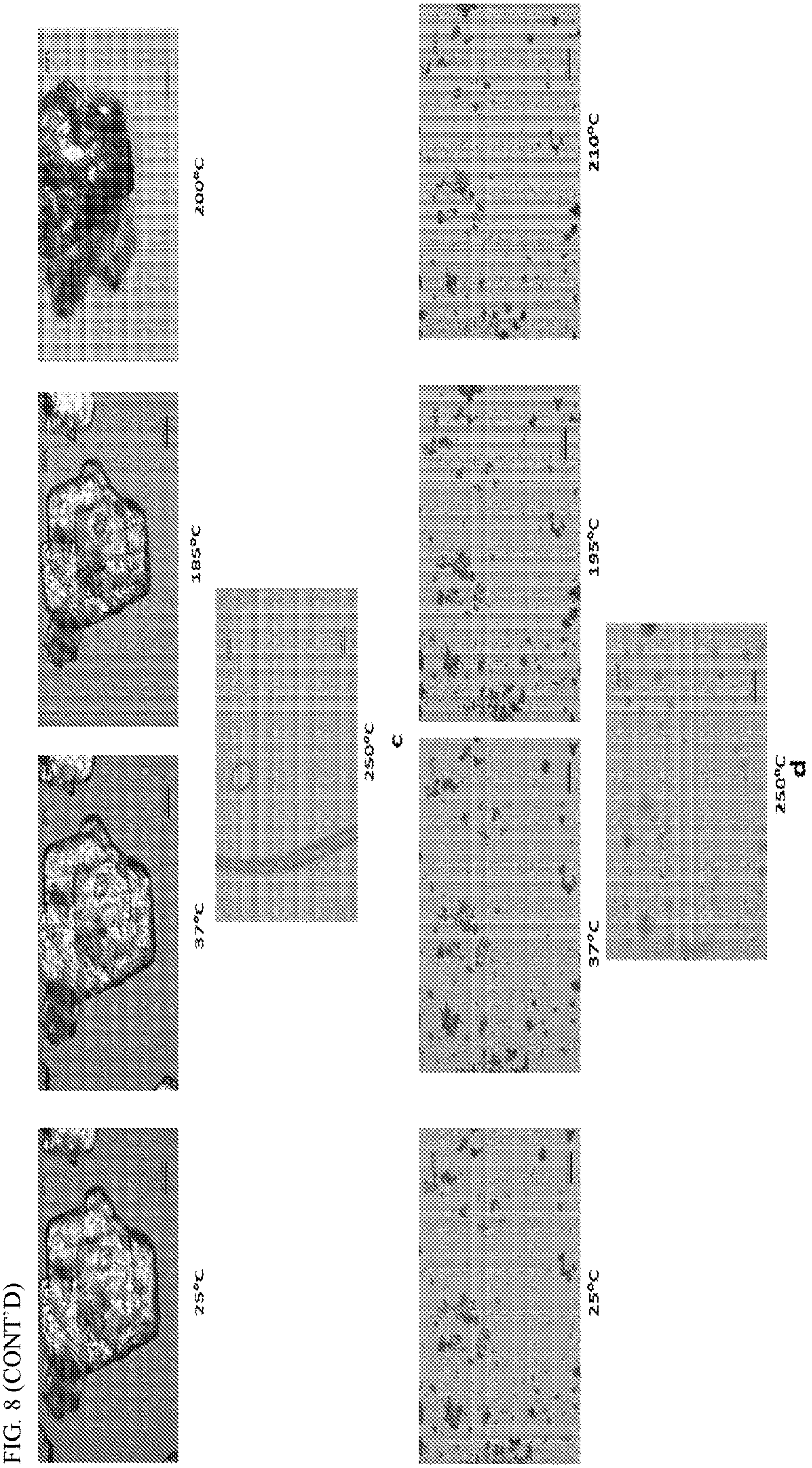
Figure 9:
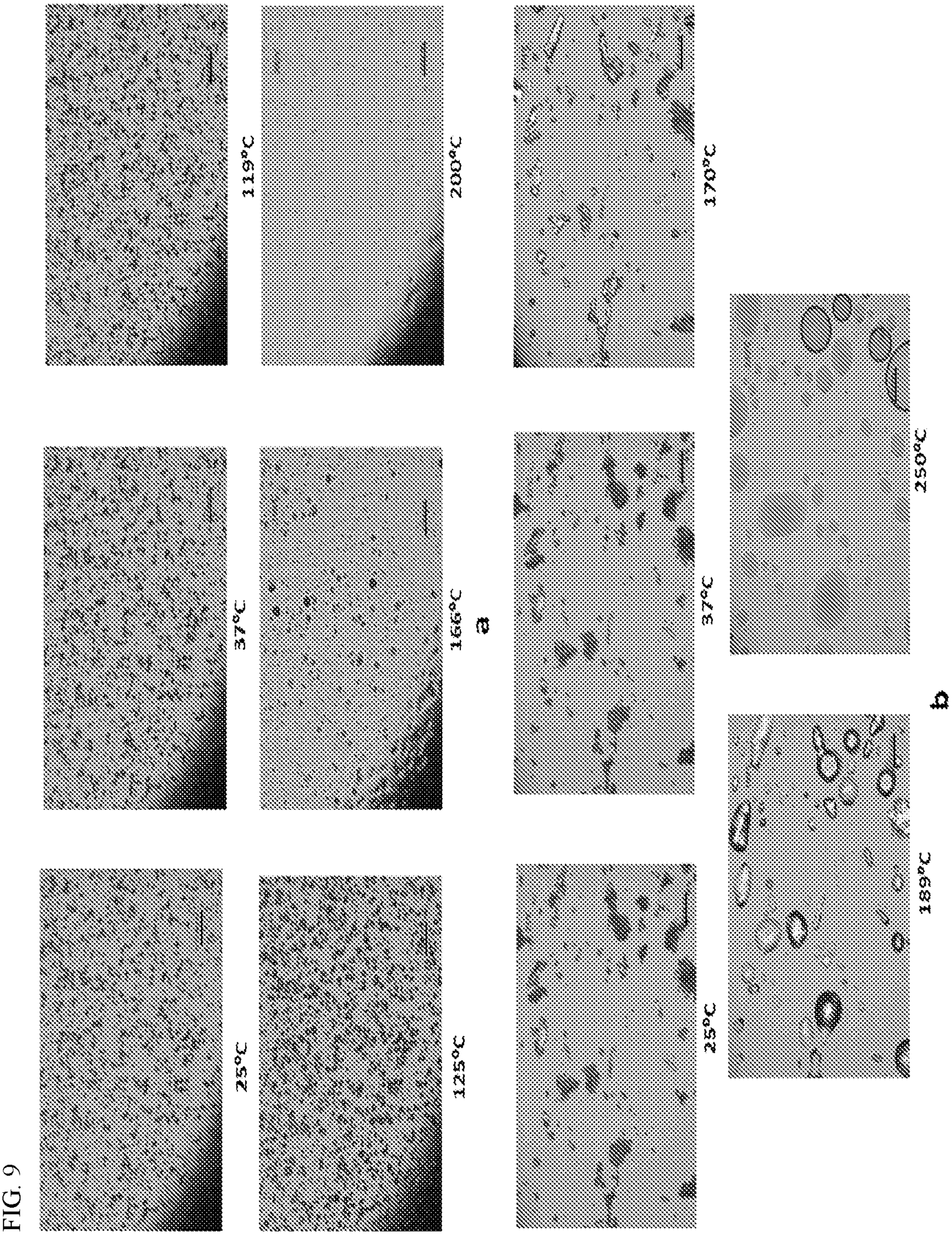

Representative images from HSM experiment are shown in FIGS. 8 and 9. Raw samples (Sim and L-Car) exhibited birefringence confirming its crystallinity. Raw Man was previously reported (Li, X., et al., J Aerosol Med Pulm Drug Deliv, 2014. 27(2): p. 731 81-93; Muralidharan et al., supra). Raw Sim exhibits some thermal events before the main thermal event corresponding to the melting of the drug (e.g., an order-to-disorder phase transition) from the solid-state to the liquid state. Raw L-Car started melting at about 195° C. and completed melting at about 205° C. SD Sim (25% and 50% PR) also shows birefringence, which confirms the retention of crystallinity after Spray Drying. Some thermal changes, which appear to be local melting, are displayed approximately between 80° C. and 100° C. and then the main thermal event at about 125° C. corresponding to the melting of the drug where birefringence disappears and droplets are formed due to the phase transition from solid to liquid. SD L-Car (25% and 50% PR) shows birefringence, as well. Only one thermal event starting from about 195° C. and ending at about 210° C. is seen (melting of the powder).

Birefringence is observable in all Co-SD systems ratifying the retention of crystallinity and melting of the powders is clearly seen at about 120° C. Also, localized melting is observed in Co-SD systems at about 100° C. to 110° C. Co-SD 484 of Sim with Man and about 180° C. in Sim with L-Car.

Attenuated Total Reflectance Fourier Transform Infrared Spectroscopy (ATR-FTIR)

Figure 10:
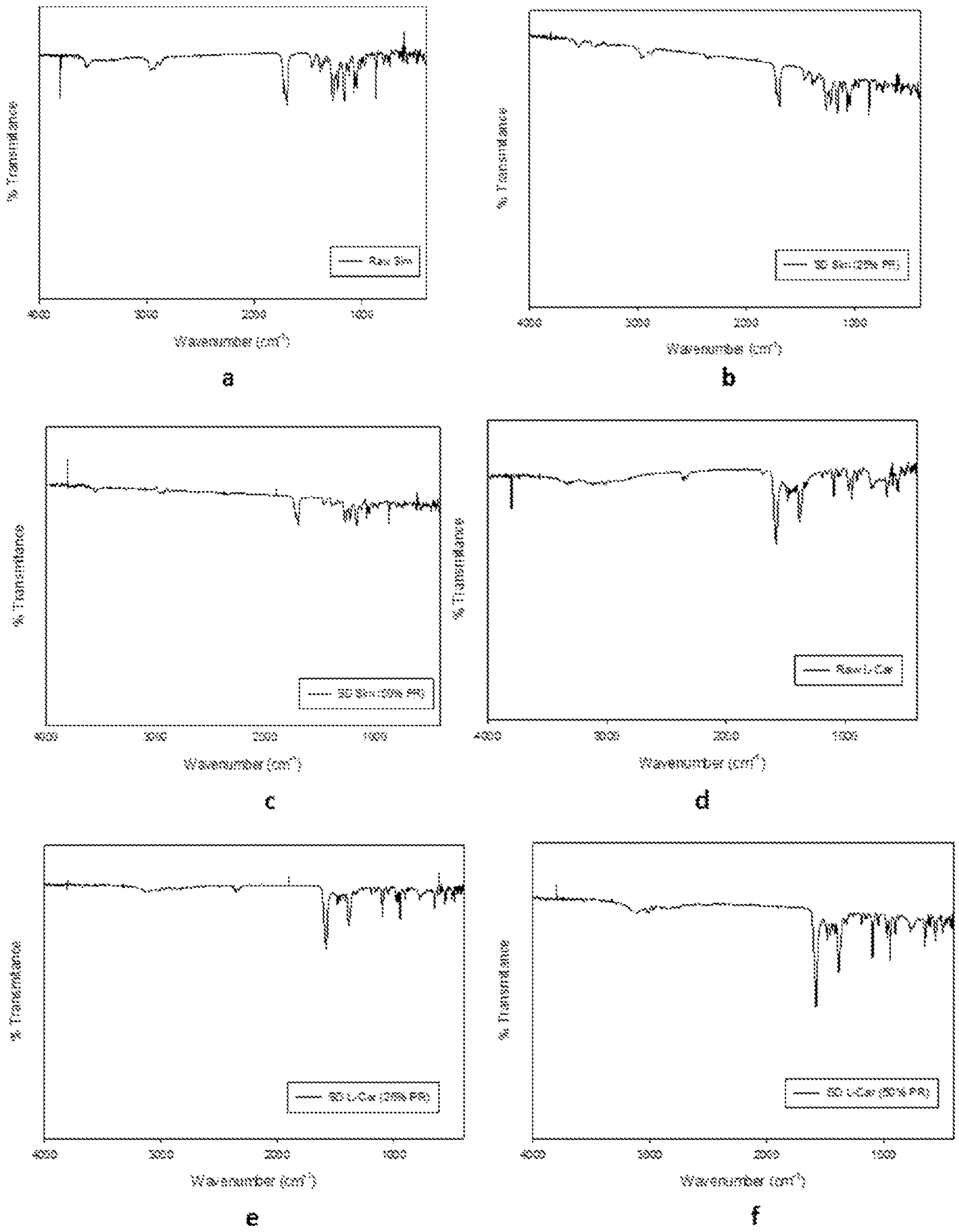
Figure 10:
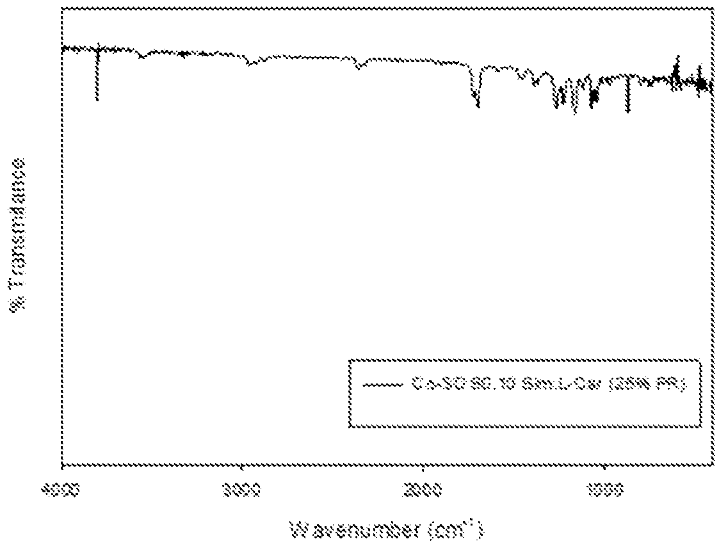
Figure 11:
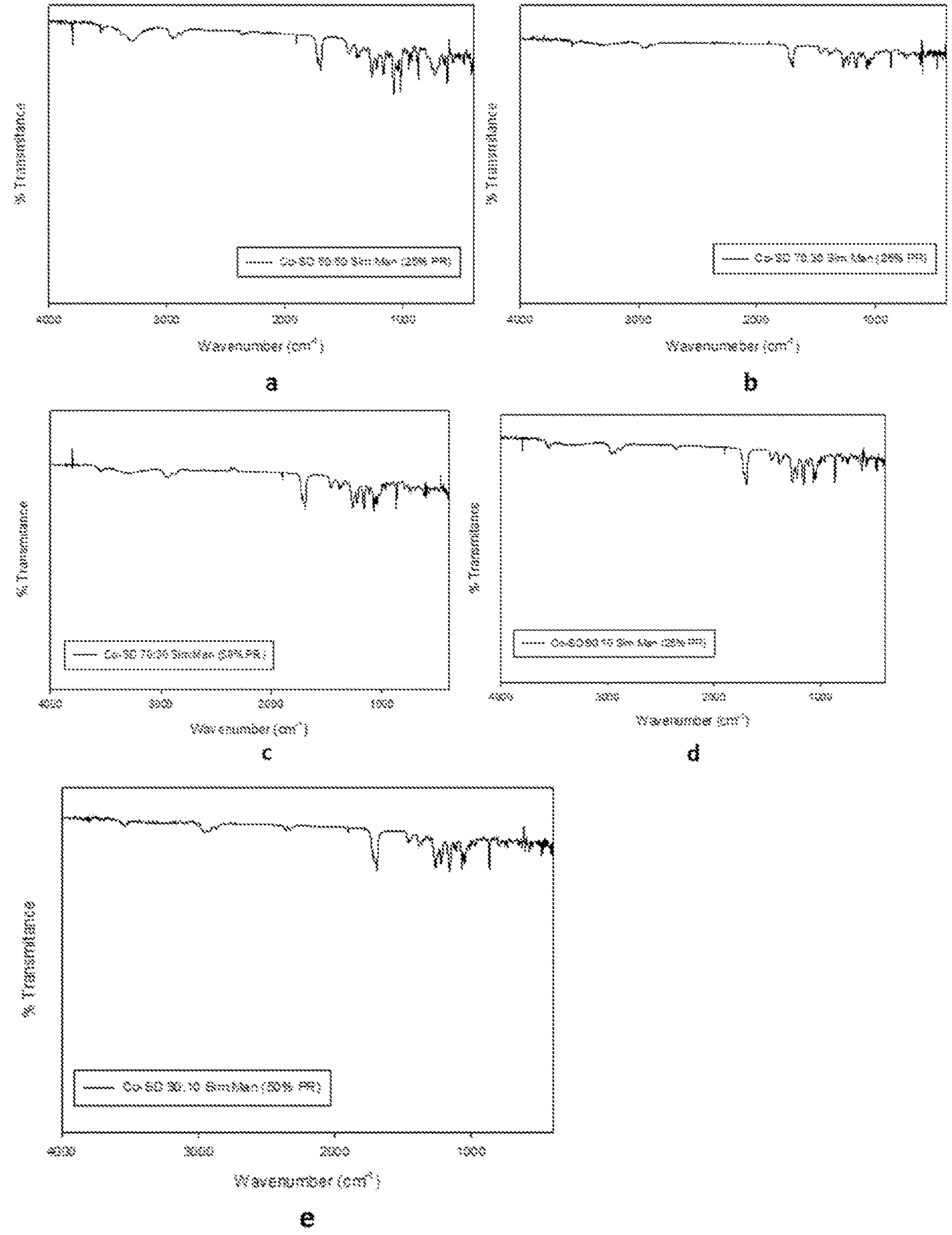
FIG. 11. ATR-FTIR spectra for Co-SD powders of Sim and Man: (a) Co-SD 50:50 Sim:Man (25% PR); (b) Co-SD 70:30 Sim:Man (25% PR); (c) Co-SD 70:30 Sim:Man (50% PR); (d) Co-SD 90:10 Sim:Man (25% PR); (e) Co-SD 90:10 Sim:Man (50% PR)

Formulated particles and their raw counterparts were subjected to ATR-FTIR analysis to define the functional groups present in the system, as shown in FIGS. 10 and 11. The ATR-FTIR spectra of Raw Sim is in accordance with what is previously reported (Singh, H., B. et al., Journal of Pharmaceutical Research: IJPR, 2012. 11(2): p. 433-445). The following peaks are shown in FIG. 10*a:* 3564, 2964, 2872, 1722, 1164, 1066 cm-1 (Singh et al., supra). Raw L-Car is also in good agreement with the literature, showing characteristics peaks at: 1580, 1483, 141, 1383, 968, 946 and 774 cm-1 (Podstawka, E., et al., Journal of Raman Spectroscopy, 2007. 38(3): p. 356-363) and Man spectra also correspond with previously reports (Li, X., et al., J Aerosol Med Pulm Drug Deliv, 2014. 27(2): p.731 81-93). FTIR spectra of Co-SD powders confirm the presence of the respective components.

Raman Spectroscopy

Figure 12A:
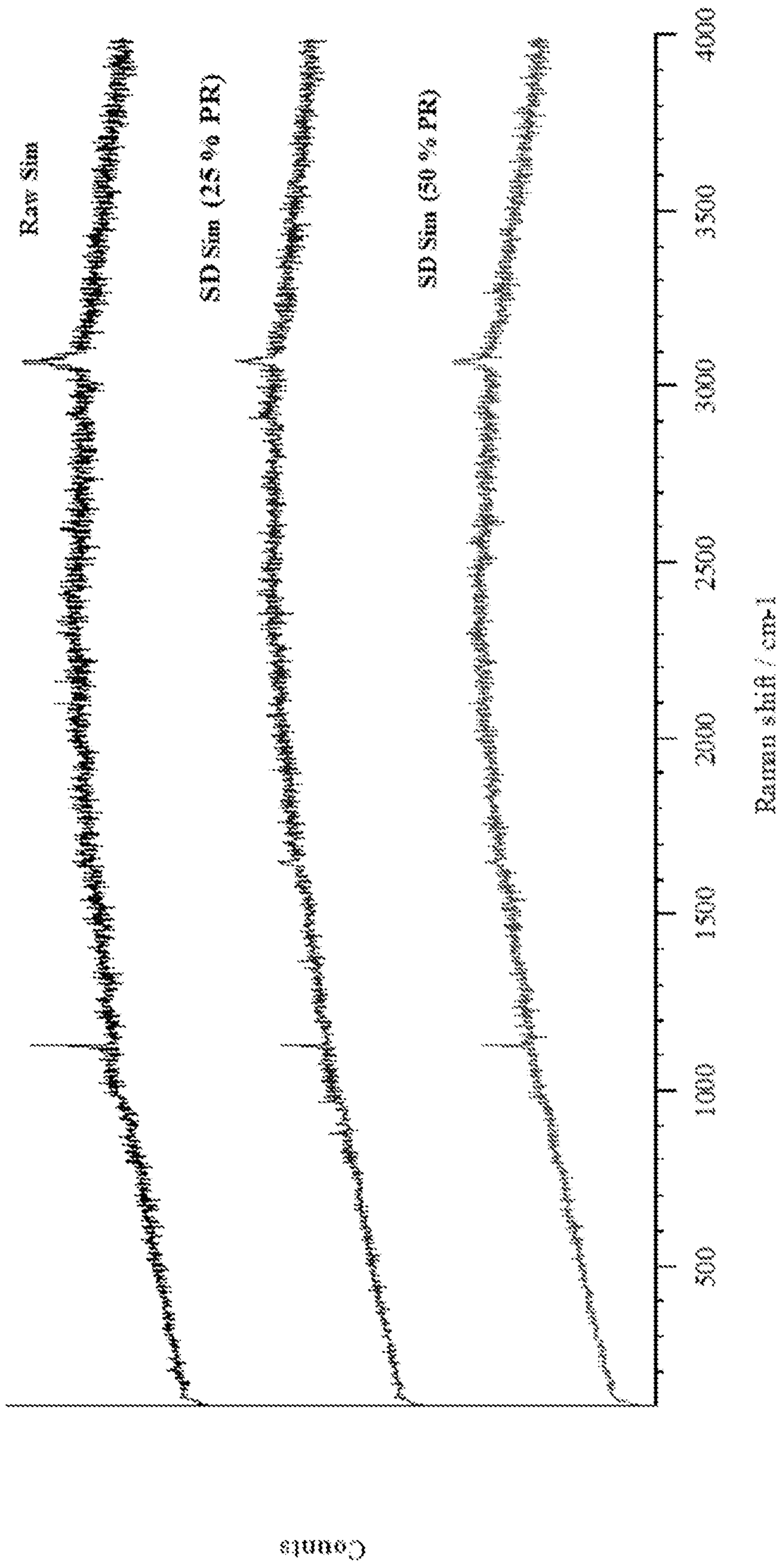
FIG. 12. Raman Spectra of Raw and SD particles for: (a) Sim; (b) L-Car
Figure 12B:
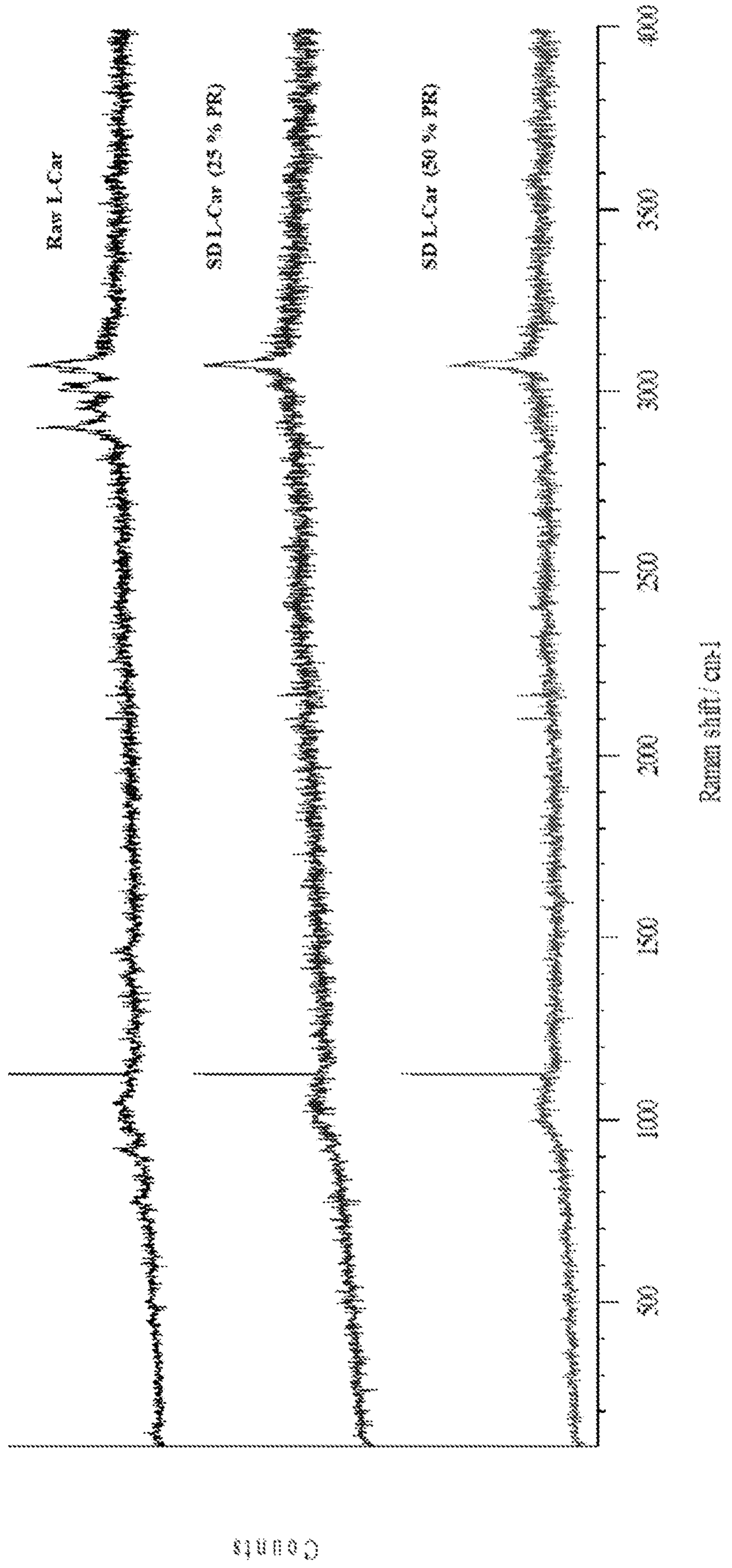
Figure 13A:
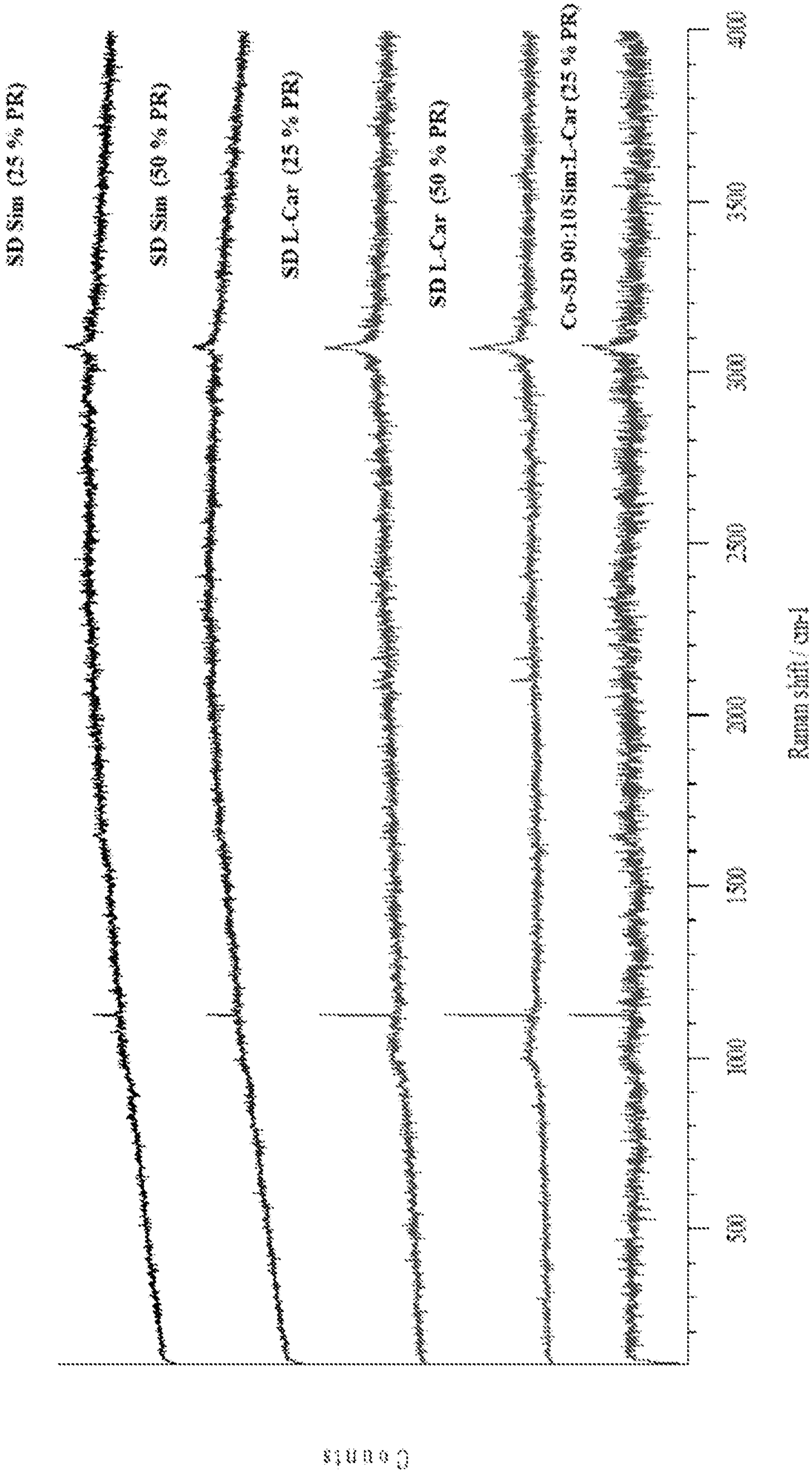
FIG. 13. Raman Spectra of SD and Co-SD particles for: (a) Sim with L-Car; (b) Sim with Man FIG. 14. In vitro aerosol deposition using the NGI™ and the FDA-approved human HandiHaler® DPI device under FDA/USP-required condition.
Figure 13B:
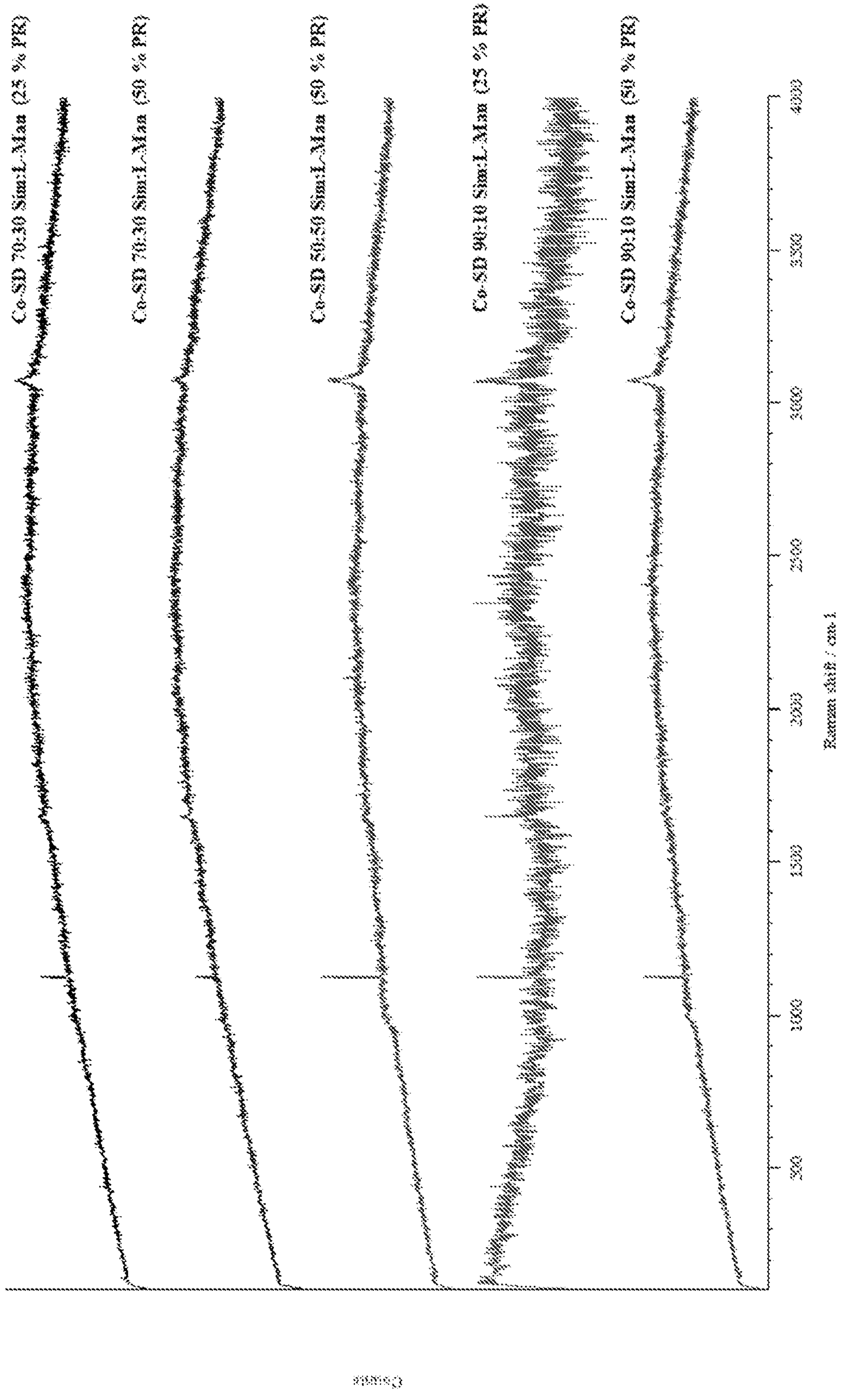
Figure 14:
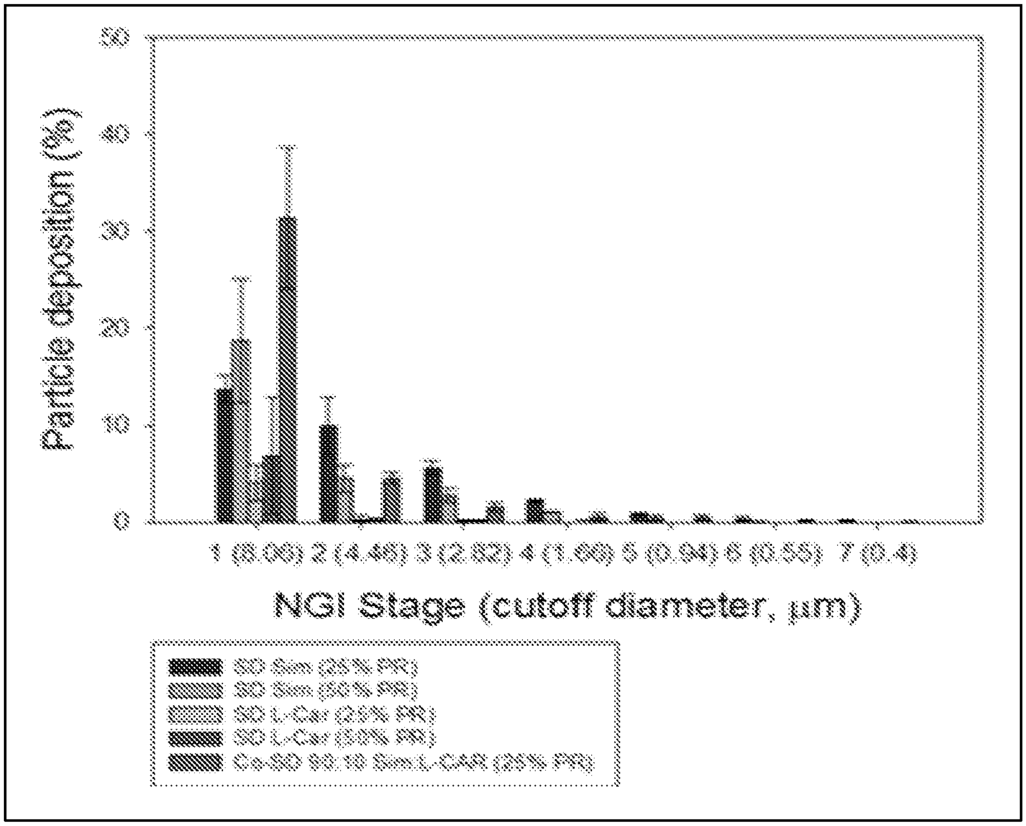
Figure 15:
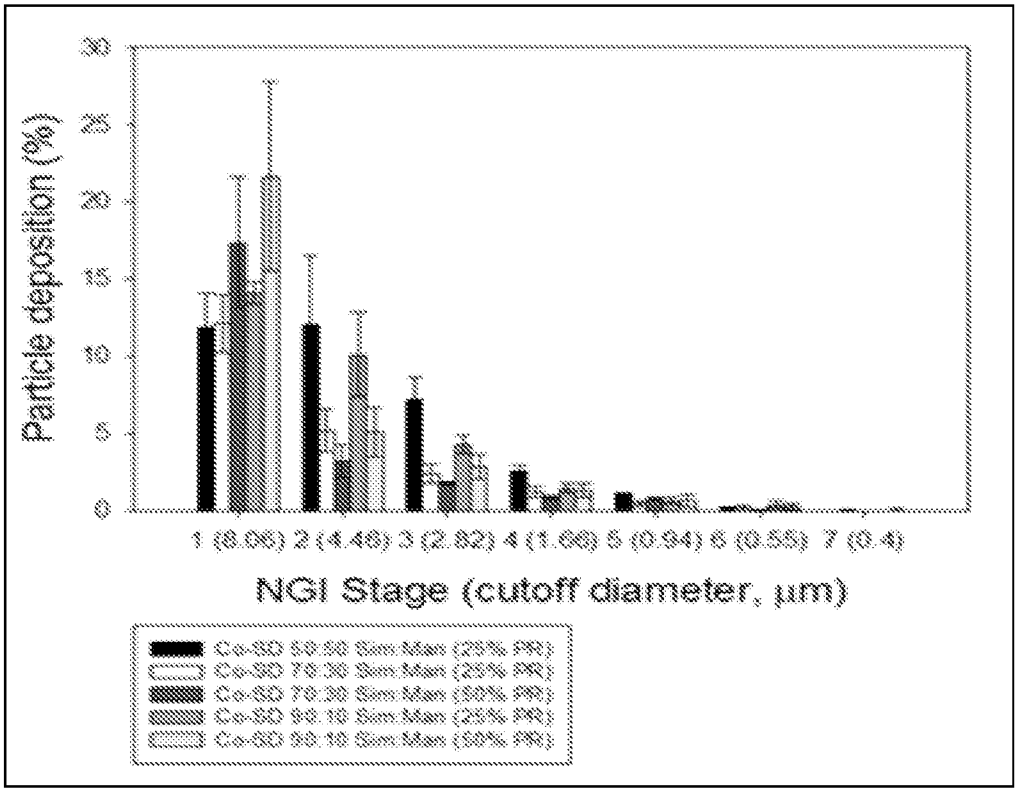
FIG. 15. In vitro aerosol deposition using the NGI™ and the FDA-approved human HandiHaler® DPI device under FDA/USP-required condition.

Raman spectroscopy was performed in order to confirm the presence of the components in all formulations. A spectral scan from 100-4000/cm-1 at 1% laser power and 10 seconds of exposure was performed on all samples to avoid fluorescence. Raman spectra of all raw, SD and Co-SD systems are shown in FIGS. 12 and 13. Raw Sim shows characteristic Raman shift at 1123, 1648 and 3074 cm-1, as well as SD Sim (25% and 50% PR). This is in good agreement with what is reported (Graeser, K. A., et al., Crystal Growth & Design, 2008. 8(1): p. 128-135). Raw L-Car shows characteristic Raman shift at 1123, 2903, 3008 and 3075 cm-1. The Raman spectra of SD L-Car (25% and 50% PR) shows a change. Raman shift at 1123, 2103 and 3075 cm-1 are shown. Co-SD Sim with L-Car shows a Raman shift at 507 1123, 1649 and 3081 cm-1. Raw Man, as previously reported, (Muralidharan et al., supra) shows characteristic Raman shift at 876, 1037, 2912, 2953, 2972, 2989, 3226 and 3397 cm-1. All Co-SD systems of Sim with Man show Raman shift at 1123, 1645, and 3078 cm-1. All SD and Co-SD systems showed high crystallinity, which is in good agreement with XRPD, DSC and HSM data presented above.

In Vitro Aerosol Dispersion Performance

In vitro aerosol dispersion performance was successfully performed using NGI®. The comprehensive aerosol dispersion performance parameters for SD Sim and L-Car and the Co-SD systems are listed in Table 5. In general, all the systems had more than 70% of the dose emitted from the device with the exception of both SD L-Car systems, which presented low emitted doses from the device. Overall lower pump rates (25%) exhibited better aerosol dispersion performance. With this pump rate deposition on stage 1 was decreased and deposition on stage 7 was achieved. The Co-SD systems with Man had improved aerosol dispersion performance. 50:50 and 90:10 molar ratios were the best systems at 25% pump rate. These two systems had a smaller amount of powder deposition on stages 1-3 and a greater amount of powder deposition on lower stages including stage 7. Co-SD system of Sim with L-Car showed deposition in stages 1-6, but the absence of deposition on stage 7.

In Vitro Cell Dose Response Assay

Figure 16:
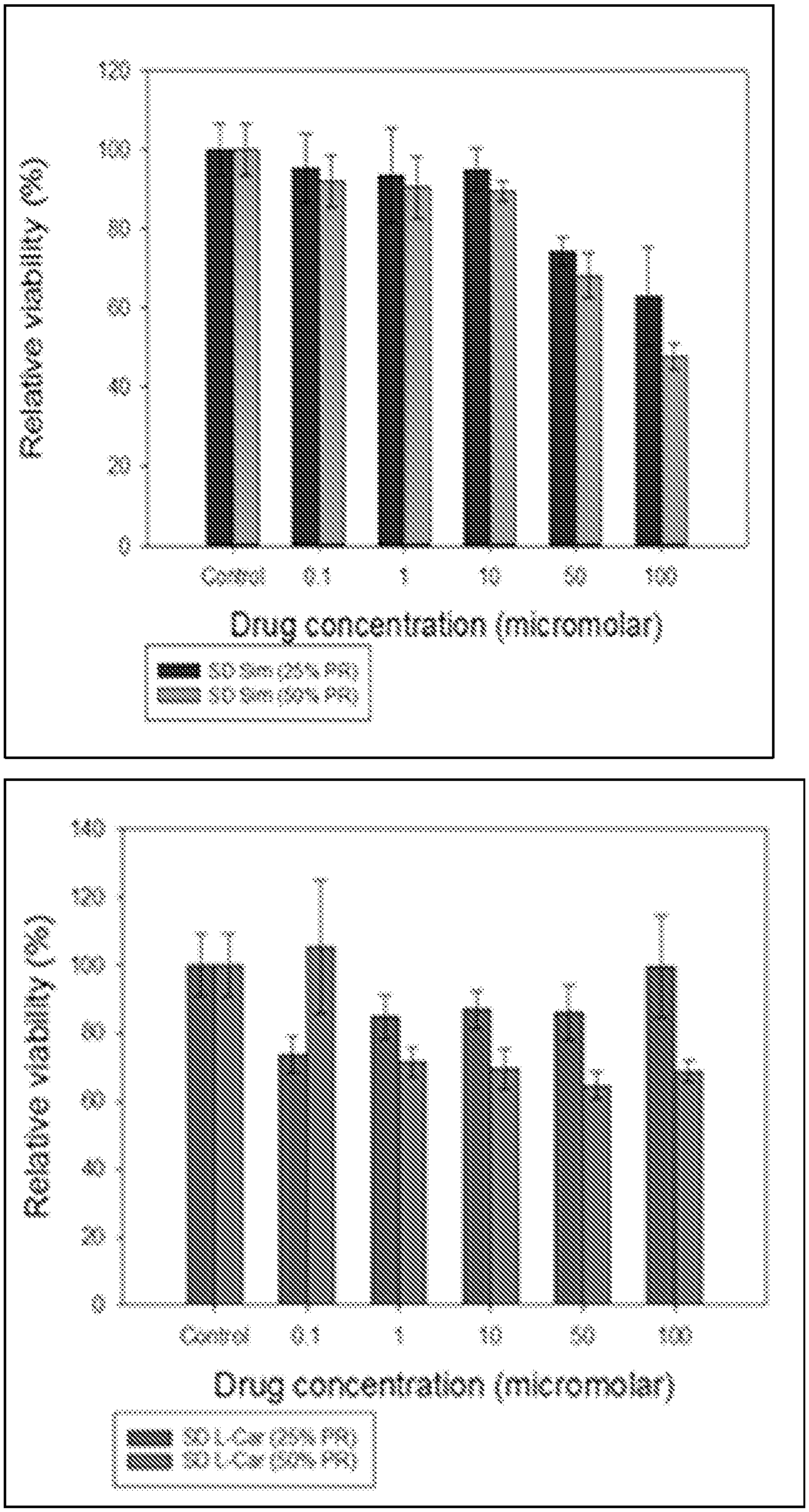
FIG. 16. In vitro drug dose-response graphs for human H358 bronchioalveolar pulmonary cells after 72 hours of exposure to different concentrations of SD and Co-SD particles of Sim, L-Car, Sim:L-Car and Sim:Man. (n=6, Mean±SD).
Figure 16:
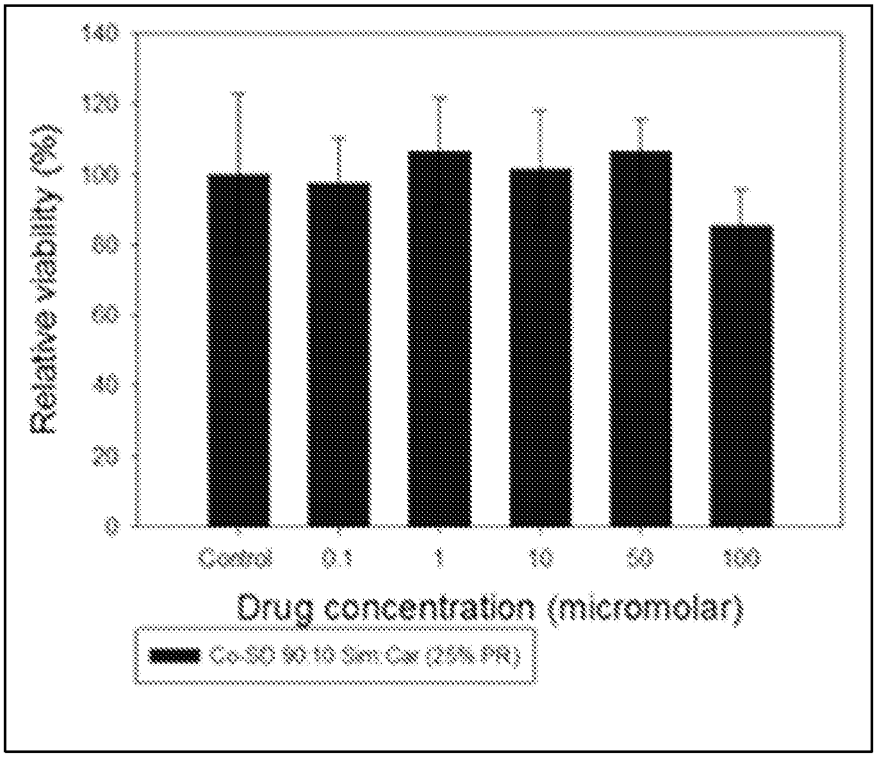
Figure 16:
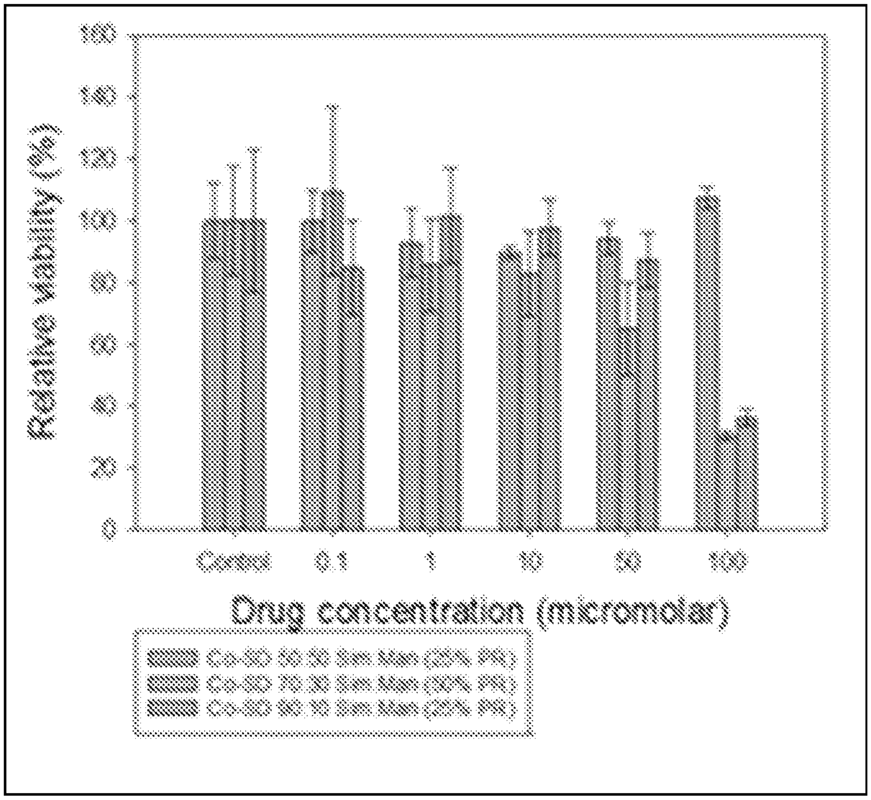
Figure 17:
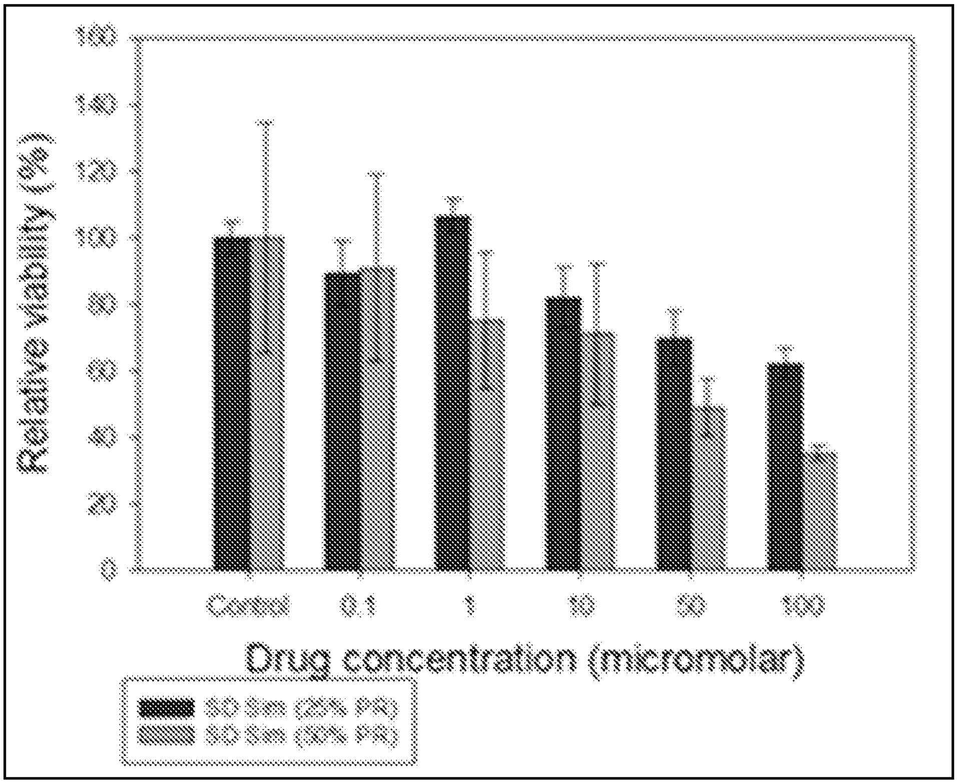
FIG. 17. In vitro drug dose-response graphs for human A549 alveolar pulmonary cells after 72 hours of exposure to different concentrations of SD and Co-SD particles of Sim, L-Car, Sim:L-Car and Sim:Man. (n=6, Mean±SD).
Figure 17:
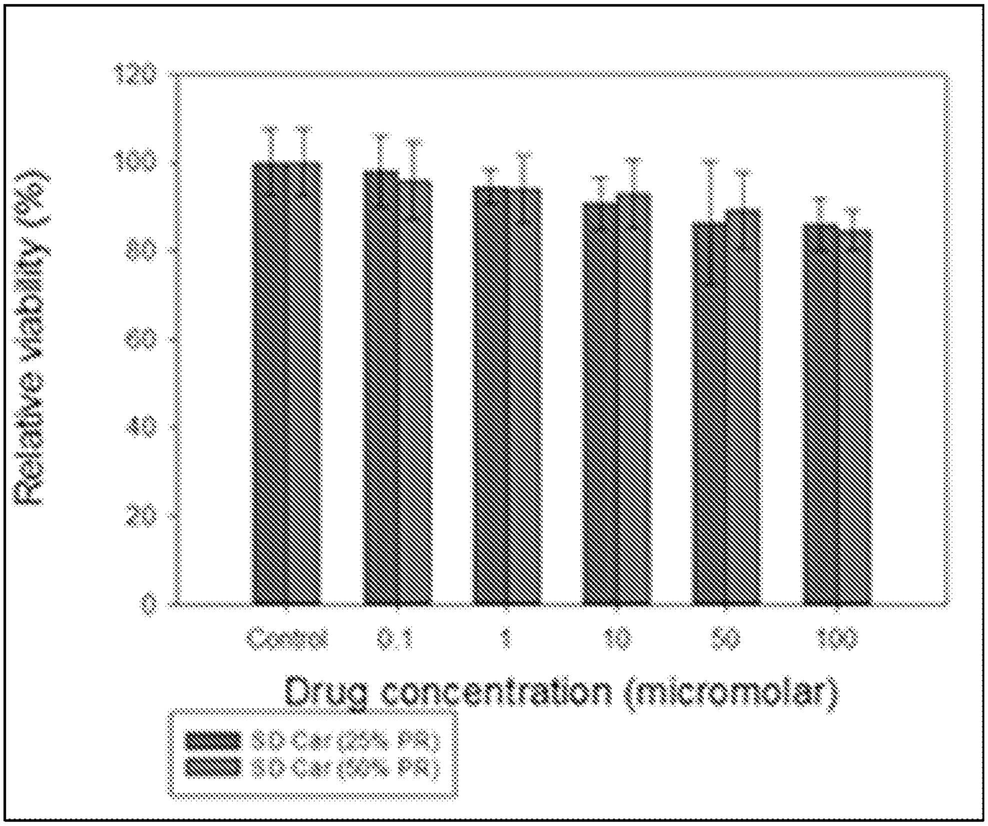
Figure 17:
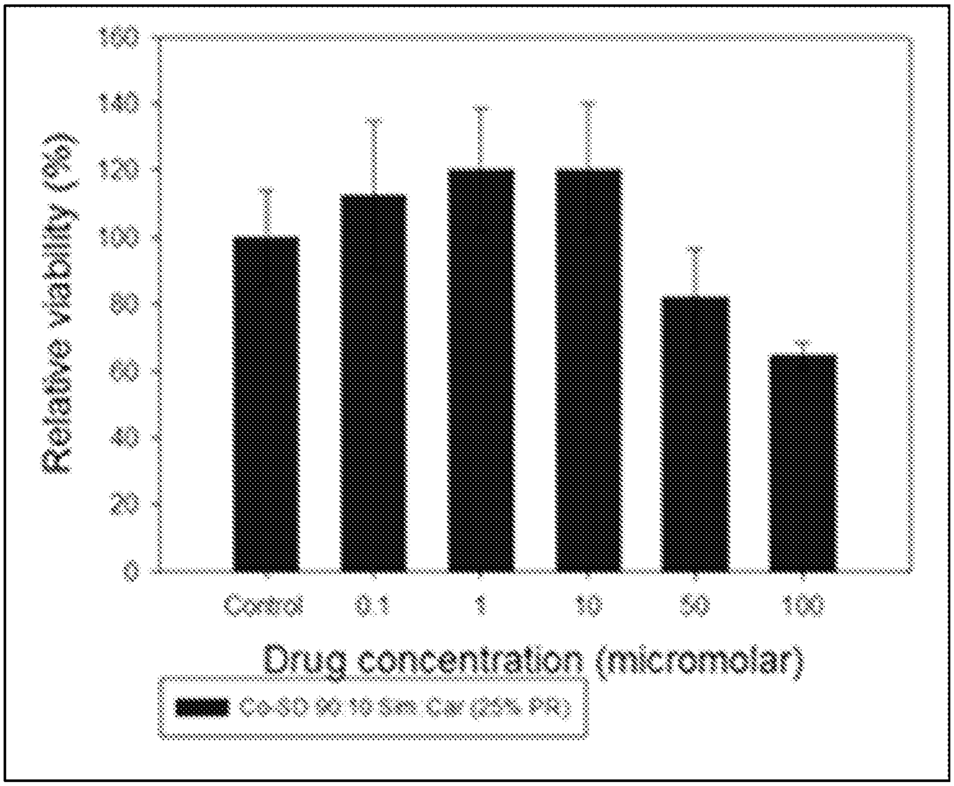
Figure 17:
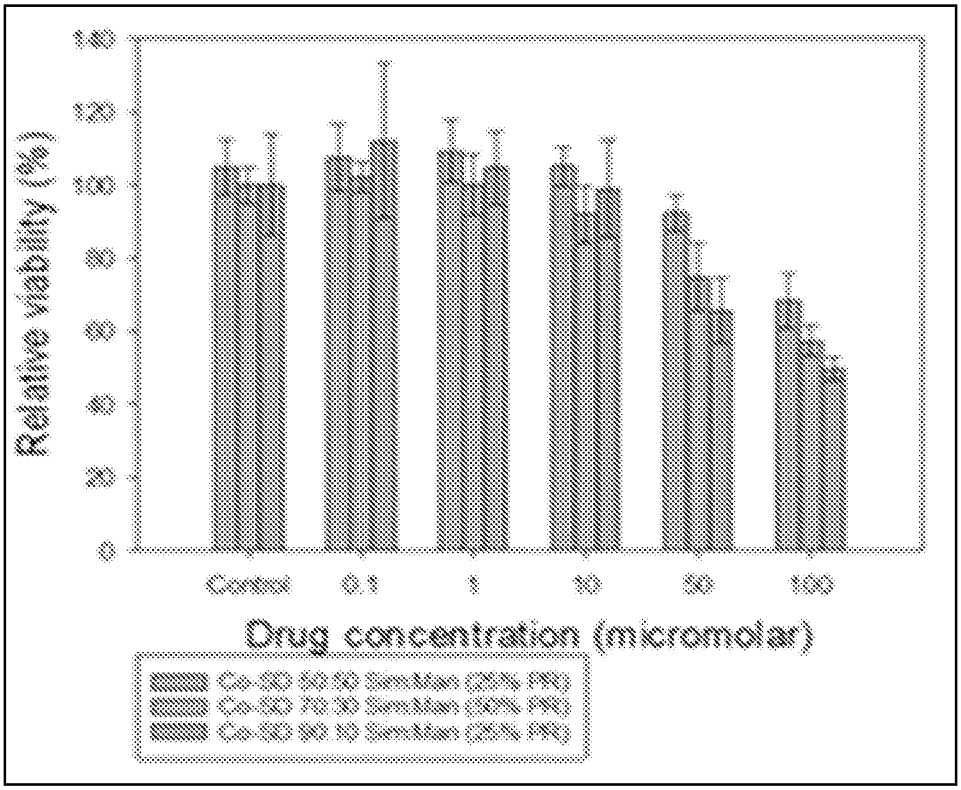
Figure 18:
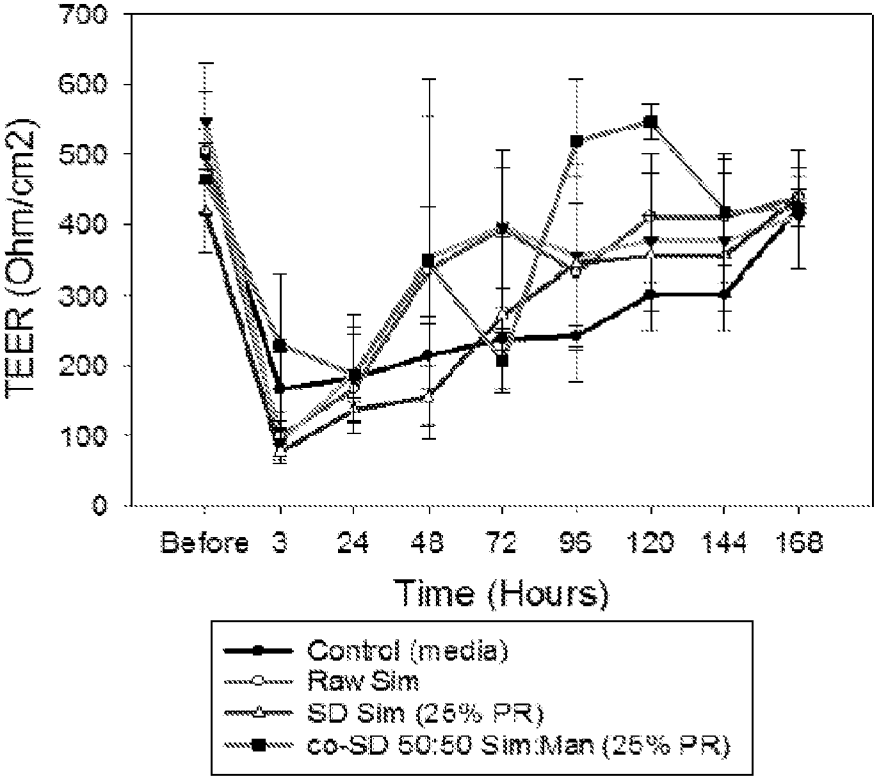
FIG. 18. Transepithelial electrical resistance (TEER) analysis of human Calu-3 lung epithelial cells exposed to SD and Co-SD particles containing Sim, L-Car and Man in air-interface culture (AIC) conditions at 37° C. (n=3, mean±SD).
Figure 18:
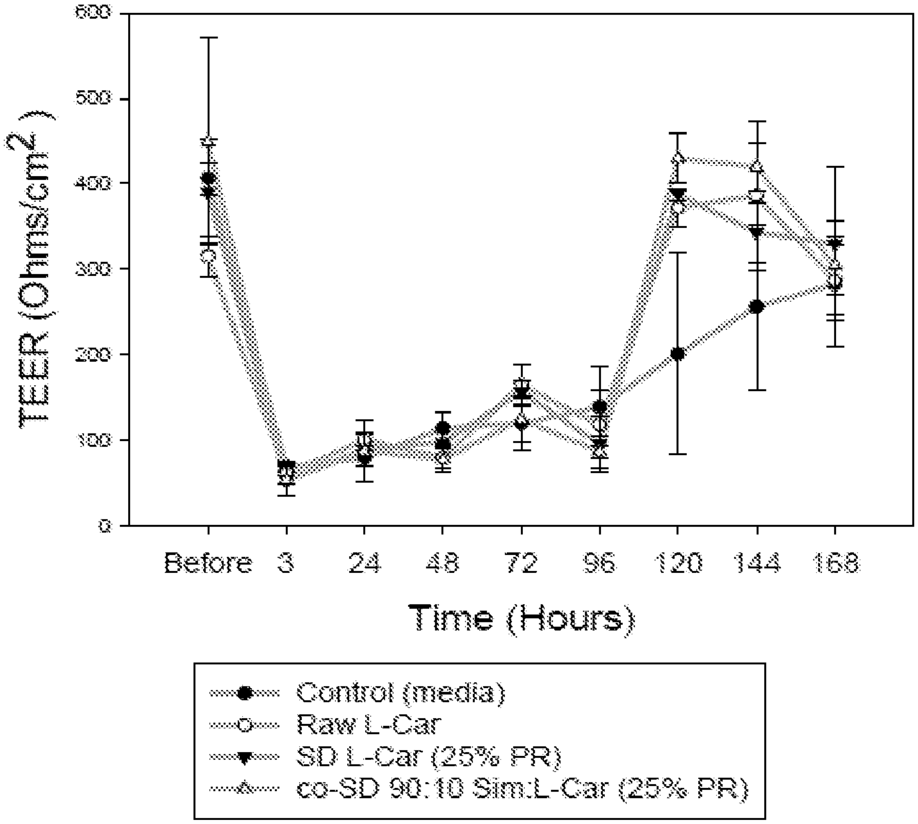

Different concentration of SD and Co-SD formulations were exposed to H358 and A549 cells in order to test the dose-response of these particles. FIG. 16 shows the dose response of H358 cells after 72 hours of exposure to different formulations. All formulations tested were safe at concentrations of 0.1 μM, 1 μM, and 10 μM. However, at concentrations of 50 μM and 100 μM, the relative viability of the H358 cells decreased significantly, presenting a statistically significant difference between the relative viability of the control cells (no treatment) and the relative viability of the cells exposed to the different formulations (p values<0.05). The same trend is seen in FIG. 17, when A549 cells were exposed for 72 hours to the same SD and Co-SD formulations. At concentrations of 0.1 μM, 1 μM, and 10 μM, the cells are safe, not showing a statistically significant difference between the control cells (no treatment) and the cells exposed to the formulations (p values>0.05). This is not the case in A549 cells exposed to formulations at concentrations of 50 μM and 100 μM, in which the relative viability also decreased meaningfully after the exposure of the cells to the SD and Co-SD formulations at concentrations of 50 μM and 100 μM, giving a statistically significant difference (p values<0.05).

In Vitro Transepithelial Electrical Resistance (TEER) Analysis upon Particle Exposure to Lung Epithelial Cells TEER measurements were successfully performed on 550 Calu-3 cells in AIC conditions to determine the effect of the SD and Co-SD particles on the cells. The existence of a complete monolayer was confirmed by TEER values of approximately 500 Ω/cm2 after seven days of exposure and by the observance of the monolayer via light microscopy. As shown in FIG. 17, after 3 hours of exposure TEER values dropped significantly. After seven days of culturing it can be seen that TEER values are around 500 Ω/cm2. Moreover, there is not a statistically significant difference between the TEER values before the drug exposure and after seven days of cell culturing on each of the formulations (p values>0.05).

TABLE 1

Spray drying conditions for SD and Co-SD systems.
Spray Drying conditions

| Parameter | |
|---|---|
| Inlet Temperature | 150° C. |
| Aspirator rate | 100% (40 $m^3$/hour) |
| Pump rate | 25% (7.5 ml/min) |
| | 50% (15 ml/min) |
| | 75% (22.5 ml/min) |
| Gas Flow | 670 L/hour (55 mm Hg) |
| Feed Solution Concentration | 0.5% w/v (SD Sim and SD L-Car) |
| | 0.2% w/v (Co-SD Sim:Man) |
| | 0.5% w/v (Co-SD Sim:L-Car) |
| Solvent | Methanol |
| Atomizer and Drying gas | UHP Nitrogen |
| Nozzle type and diameter | Stainless steel (0.7 mm) |

TABLE 2

Summary of the Outlet Temperatures for 909 Organic Solution Advanced Co-Spray Drying in Closed-Mode Conditions Spray Drying

| System Composition | Outlet T (° C.) |
|---|---|
| SD Sim (25% P) | 86-89 |
| SD Sim (50% P) | 71-72 |
| SD Sim (75% P) | 62-65 |
| SD L-Car (25% P) | 75-78 |
| SD L-Car (50% P) | 62-65 |
| Co-SD 90:10 Sim:L-Car (25% P) | 86 |
| Co-SD 50:50 Sim:Man (25% P) | 77 |
| Co-SD 70.30 Sim:Man (25% P) | 88-92 |
| Co-SD 70:30 Sim:Man (50% P) | 66-69 |
| Co-SD 90:10 Sim:Man (25% P) | 76 |
| Co-SD 90:10 Sim:Man (50% P) | 65-68 |

TABLE 3

Particle size. (n = 100, Mean ± SD).

| System | Mean (μm) | Range (μm) |
|---|---|---|
| Raw Sim | 20.063 ± 9.282 | 4.559-29.137 |
| SD Sim (25% PR) | 10 ± 2.91 | 4.89-20.37 |
| SD Sim (50% PR) | 7.84 ± 2.36 | 0.35-13.69 |
| Raw L-Car | 659.05 ± 235.82 | 298.38-1810.57 |
| SD L-Car (25% PR) | 15.15 ± 5.23 | 7.36-33.1 |
| SD L-Car (50% PR) | 12.64 ± 4.77 | 5.49-28.14 |
| Co-SD 90:10 Sim:L-Car (25% PR) | 11.77 ± 4.44 | 6.265-32.89 |
| Co-SD 50:50 Sim:Man (25% PR) | 7.55 ± 2.51 | 0.137-16.15 |
| Co-SD 70:30 Sim:Man (25% PR) | 10.53 ± 2.95 | 4.92-18.02 |
| Co-SD 70:30 Sim:Man (50% PR) | 13.34 ± 6.17 | 6.13 ± 45.4 |
| Co-SD 90:10 Sim:Man (25% PR) | 9.89 ± 2.72 | 3.53-17.71 |
| Co-SD 90:10 Sim:Man (50% PR) | 8.94 ± 2.93 | 4.219-18.22 |

TABLE 4

Phase Transition Temperature (Tpeak). Values for Various 948 SD and Co-SD Sim with Man and L-Car Dry Powder Inhalation Formulations (n = 3, Mean ± SD).

| | Exotherm | | Endotherm | | Endotherm | |
|---|---|---|---|---|---|---|
| | Tpeak (° C.) | Enthalpy (J/g) | Tpeak (° C.) | Enthalpy (J/g) | Tpeak (° C.) | Enthalpy (J/g) |
| **Raw and SD** | | | | | | |
| Raw Sim | 129.5 ± 0.11 | 5.94 ± 0.72 | 135.95 ± 0.62 | 62.04 ± 8.05 | | |
| Raw Man | | | 166.27 ± 0.14 | 347.83 ± 24.8 | | |
| Raw Car | | | 191.26 ± 1.37 | 524.83 ± 139 | | |
| SD Sim (25% P) | 120.69 ± 0.47 | 31.24 ± 3.12 | 131.46 ± 1.02 | 23.02 ± 9.27 | | |
| SD Sim (50% P) | 120.08 ± 0.52 | 22.04 ± 3.72 | 133.33 ± 0.79 | 40.38 ± 6.97 | | |
| SD L-Car (25% P) | | | 195.1 ± 1.61 | 580.73 ± 66 | | |
| SD L-Car (50% P) | | | 193.61 ± 1.19 | 598.83 ± 12.67 | | |
| **Co-SD Sim:L-Car Molar Ratio** | | | | | | |
| 90:10 Sim:L-Car (25% P) | | | 130.30 ± 0.30 | 37.43 ± 5.22 | | |
| **Co-Sim Sim:Man Molar Ratio** | | | | | | |
| 50:50 Sim:Man (25% P) | 120.62 ± 0.15 | 28.40 ± 0.28 | 127.15 ± 1.61 | 14.45 ± 1.18 | 163.92 ± 0.18 | 89.58 ± 1.29 |
| 70:30 Sim:Man (25% P) | 126.17 ± 0.65 | 7.13 ± 1.21 | 130.99 ± 1.16 | 34.82 ± 5.94 | 163.82 ± 0.19 | 40.24 ± 2.08 |
| 70:30 Sim:Man (50% P) | 121.6 ± 3.45 | 9.17 ± 3.50 | 132.31 ± 0.05 | 37.74 ± 6.82 | 163.8 ± 0.16 | 42.66 ± 0.92 |
| 90:10 Sim:Man (25% P) | 119.30 ± 0.36 | 28.56 ± 4.60 | 129.60 ± 1.08 | 15.69 ± 8.36 | 163.05 ± 0.12 | 42.66 ± 0.92 |
| 90:10 Sim:Man (50% P) | 116.41 ± 1.82 | 18.03 ± 5.34 | 131.61 ± 1.41 | 32.03 ± 12.32 | 163.07 ± 0.27 | 6.05 ± 0.55 |

TABLE 5

Residual Water Content for Various SD and Co-SD Dry Powder Inhalation Formulations as Quantified Analytically by Karl Fisher Titration (n = 3, Mean ± SD)

| SD Inhalation Powders | Water content % (w/w) |
|---|---|
| **Raw and SD** | |
| Raw Sim | 1.46 ± 0.38 |
| Raw Man | 0.3 ± 0.13 |
| Raw L-Car | 2.68 ± 0.8 |
| SD Sim (25% P) | 2.20 ± 0.19 |
| SD Sim (50% P) | 1.46 ± 0.03 |

TABLE 5-continued

Residual Water Content for Various SD and Co-SD Dry Powder Inhalation Formulations as Quantified Analytically by Karl Fisher Titration (n = 3, Mean ± SD)

| SD Inhalation Powders | Water content % (w/w) |
|---|---|
| **Co-SD Sim:L-Car Molar Ratio** | |
| 90:10 Sim:L-Car (25% P) | 2.63 ± 0.39 |
| **Co-SD Sim:Man Molar Ratios** | |
| 90:10 Sim:Man (25% P) | 0.87 ± 0.62 |
| 90:10 Sim:Man (50% P) | 0.45 ± 0.04 |
| 70:30 Sim:Man (25% P) | 0.38 ± 0.09 |
| 70:30 Sim:Man (50% P) | 0.45 ± 0.05 |
| 50:50 Sim:Man (25% P) | 0.61 ± 0.27 |

TABLE 6

In Vitro Aerosol Dispersion Performance Using the Next Generation Impactor ™ for SD and Co-SD Aerosol Systems Including Mass Median Aerodynamic Diameter (MMAD), Geometric Standard Deviation (GSD), Fine Particle Fraction FPF), Respirable Fraction (RF), and Emitted Dose (ED). (n = 3, Mean ± SD).

| System composition | ED (%) | FPF (%) | RF (%) | MMAD (μm) | GSD (μm) |
|---|---|---|---|---|---|
| SD Sim (25% P) | 84.33 ± 4.79 | 18.40 ± 3.16 | 57.97 ± 1.22 | 7.38 ± 0.20 | 2.26 ± 0.23 |
| SD Sim/met (50% P) | 95.92 ± 3 | 8.80 ± 1.94 | 32.63 ± 6.31 | 12.01 ± 2.78 | 2.53 ± 0.34 |
| SD L-Car (25% P) | 50.57 ± 7.60 | 0.44 ± 0.29 | 10.20 ± 7.17 | 36.31 ± 20.91 | 2.78 ± 0.76 |
| SD L-Car (50% P) | 37.11 ± 9.38 | 0.53 ± 0.32 | 10.32 ± 9.77 | 8.4 ± 8.56 | 1.76 ± 0.94 |
| Co-SD 90:10 Sim:L-Car (25% P) | 93.65 ± 5.53 | 6.57 ± 1.04 | 18.73 ± 3.43 | 19.55 ± 2.52 | 2.75 ± 0.74 |
| Co-SD 50:50 Sim:Man (25% P) | 100 ± 0 | 26.07 ± 4.245 | 65.54 ± 2.01 | 6.31 ± 0.19 | 1.95 ± 0.11 |
| Co-SD 70:30 Sim:Man (25% P) | 76.77 ± 3.66 | 9.15 ± 1.55 | 43.64 ± 7.12 | 9.86 ± 1.13 | 2.52 ± 0.41 |

TABLE 6-continued

In Vitro Aerosol Dispersion Performance Using the Next Generation Impactor™ for SD and Co-SD Aerosol Systems Including Mass Median Aerodynamic Diameter (MMAD), Geometric Standard Deviation (GSD), Fine Particle Fraction FPF), Respirable Fraction (RF), and Emitted Dose (ED). (n = 3, Mean ± SD).

| System composition | ED (%) | FPF (%) | RF (%) | MMAD (μm) | GSD (μm) |
|---|---|---|---|---|---|
| Co-SD 70:30 Sim:Man (50% P) | 70.93 ± 10.09 | 6.56 ± 0.86 | 27.62 ± 4.05 | 15.46 ± 3.17 | 3.07 ± 0.34 |
| Co-SD 90:10 Sim:Man (25% P) | 100 ± 0 | 17.57 ± 3.36 | 54.11 ± 2.86 | 7.29 ± 1.04 | 2.07 ± 0.08 |
| Co-SD 90:10 Sim:Man (50% P) | 89.84 ± 5.52 | 10.40 ± 3.16 | 31.7 ± 1.88 | 13.28 ± 0.84 | 2.89 ± 0.31 |

Example 2

Figure 19:
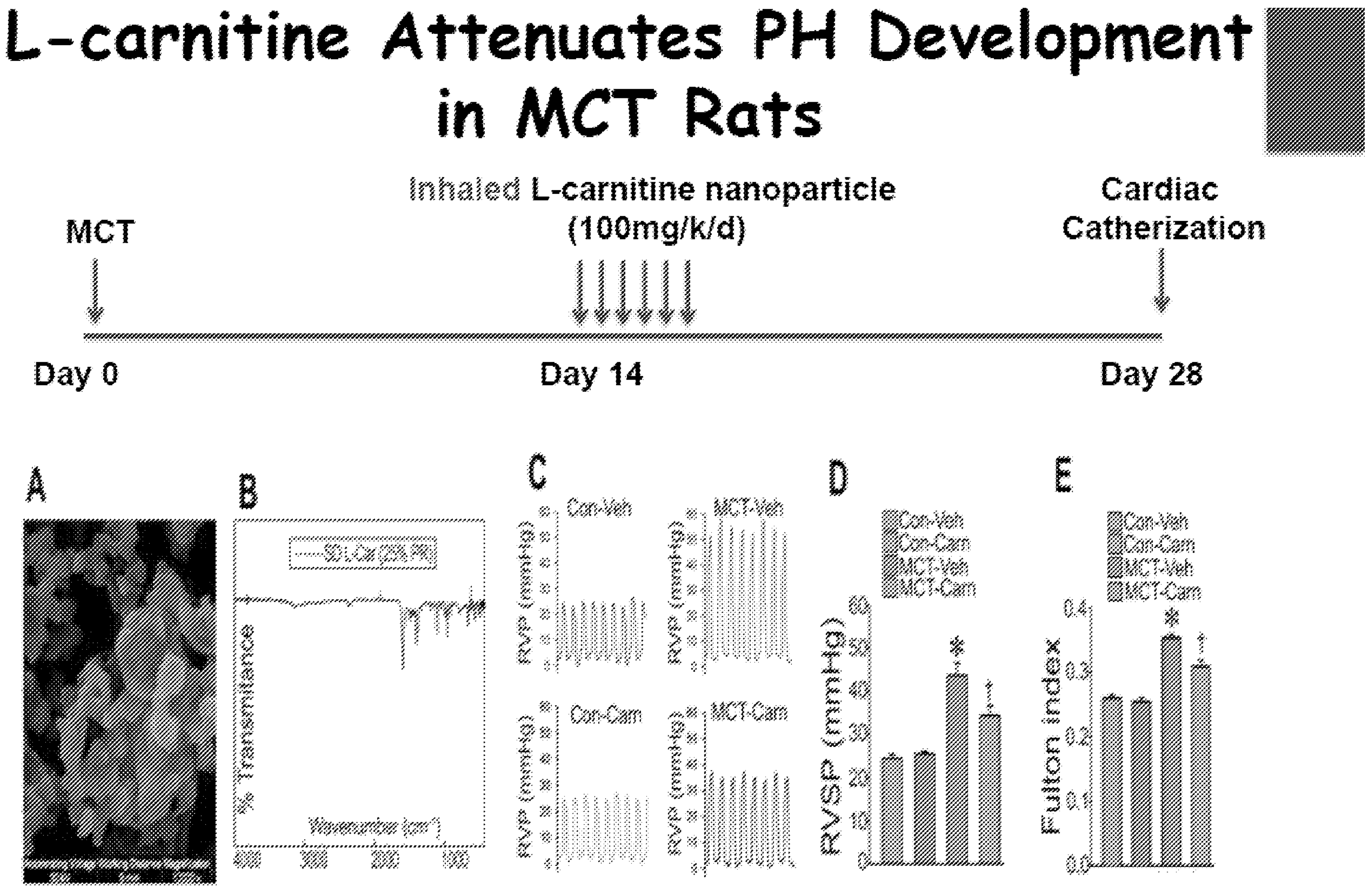
FIG. 19. L-Car attenuates PH development in MCT rats.
Figure 20:
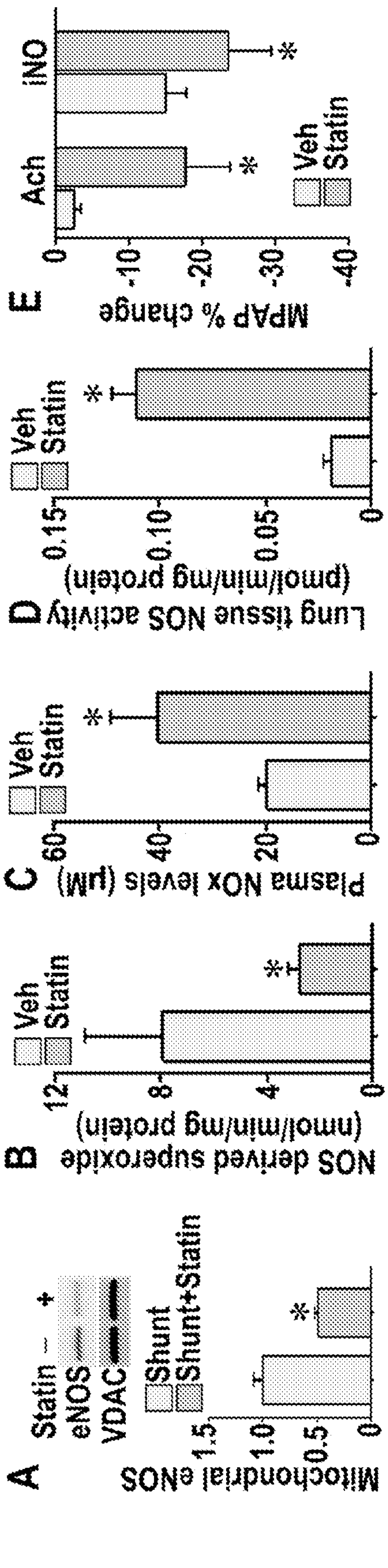
FIG. 20. Simvastatin attenuates the mitochondrial translocation of eNOS and preserves endothelial function in lambs with increased PBF. EPR identifies a reduction in NOS-derived superoxide in Shunt lambs treated with simvastatin (B). Plasma $NO_x$ (measured using an NO analyzer) and NOS activity (determined using $^3$H-L-arginine to $^3$H-L-citrulline conversion) are increased in simvastatin treated Shunt lambs (C & D). Simvastatin also preserves endothelial function in Shunt lambs as demonstrated by a reduction in MPAP in response to acetylcholine (Ach, E). Data are mean±SE. N=3-4,*P<0.05 vs. vehicle treated Shunt lambs.

This Example describes in vivo data on inhaled carnitine and simvastatin. FIG. 19 shows that L-carnitine attenuates PH development in MCT rats. FIG. 20 shows Simvastatin attenuates the mitochondrial translocation of eNOS and preserves endothelial function in lambs with increased PBF. Mitochondrial extracts were prepared and subjected to Western blot analysis. There is a reduction in eNOS localized to the mitochondria in simvastatin treated Shunt lambs. EPR identifies a reduction in NOS-derived superoxide in Shunt lambs treated with simvastatin (B). Plasma NOx (measured using an NO analyzer) and NOS activity (determined using 3H-L-arginine to 3H-L-citrulline conversion) are increased in simvastatin treated Shunt lambs (C & D). Simvastatin also preserves endothelial function in Shunt lambs as demonstrated by a reduction in MPAP in response to acetylcholine (Ach, E). Data are mean+SE. N=3-4,*P<0.05 vs. vehicle treated Shunt lambs.

Figure 21:
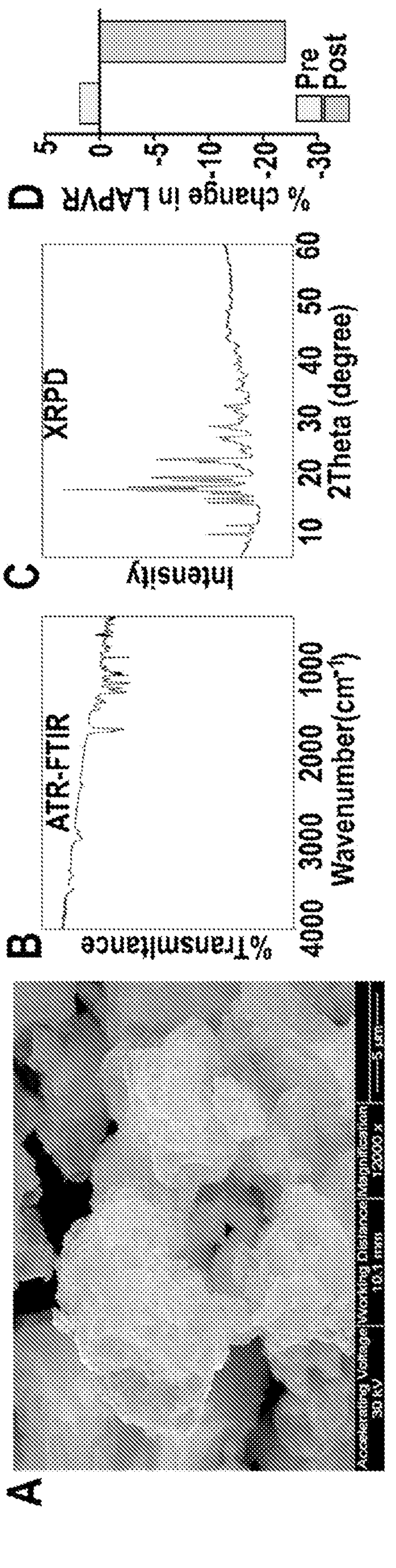
FIG. 21. Scanning electron micrograph of nanostructured respirable spray-dried particles of simvastatin drug (A)

FIG. 21 shows scanning electron micrograph of nanostructured respirable spray-dried particles of simvastatin drug (A); ATR-FTIR spectrum of nanostructured respirable spray-dried particles of simvastatin drug (B); X-ray powder diffractogram of nanostructured respirable spray-dried particles of simvastatin drug (C); and in vivo lamb data by ACh challenge for aerosolized simvastatin after one hour post-simvastatin aerosol treatment (D).

All publications and patents mentioned in the present application are herein incorporated by reference. Various modification and variation of the described methods and compositions of the disclosure will be apparent to those skilled in the art without departing from the scope and spirit of the disclosure. Although the disclosure has been described in connection with specific preferred embodiments, it should be understood that the disclosure as claimed should not be unduly limited to such specific embodiments. Indeed, various modifications of the described modes for carrying out the disclosure that are obvious to those skilled in the relevant fields are intended to be within the scope of the following claims.

We claim:

1. A composition comprising a simvastatin (Sim) particle, wherein said particle is a dry powder, wherein said Sim particle has a mass median aerodynamic diameter (MMAD) of 7.38±0.2 μm, a Fine Particle Fraction (FPF) of 18.40±3.16%, and an emitted dose (ED) of 84.33±4.79%, and wherein said particle is made by a method, comprising:

a) preparing a first solution comprising said Sim in methanol; and b) spraying said first solution using a spray drying apparatus;

and wherein said composition is suitable for delivery by inhalation.

2. A composition comprising a simvastatin (Sim) and L-carnitine (L-Car) or Sim and D-mannitol (Man) particle, wherein said particle is a dry powder, wherein said Sim and L-Car particle has a MMAD of 19.55±2.52 μm, a FPF of 6.57±1.04%, and an ED of 93.65±5.53% and said Sim and Man particle has MMAD of 6.31±0.19, 9.86±1.13, 15.46±3.17, 7.29±1.04, or 13.28±0.84 μm, a FPF of 26.07±4.245, 9.15±1.55, 6.56±0.86, 17.57±3.36, or 10.40±3.16%, and an emitted dose ED of 100, 76.77±3.36, 70.93±10.09, or 89.84±5.52%, and wherein said particle is made by a method, comprising:

a) preparing a first solution comprising said Sim in methanol and a second solution comprising L-Car or Man in methanol;

b) mixing said first and second solutions to generate a mixture; and c) spraying said mixture using a spray drying apparatus;

and wherein said composition is suitable for delivery by inhalation.

3. The composition of claim 2, wherein said-Sim and Man are present at a molar ratio of 90:10 to 10:90 Sim:Man.

4. The composition of claim 2, wherein said Sim and L-Car are present at a molar ratio of 90:10 to 10:90 Sim: L-Car.

5. A method of treating a lung disorder in a subject, comprising: administering the composition of claim 1 to a subject diagnosed with or having signs or symptoms of said lung disorder under conditions such that said signs or symptoms are reduced.

6. The method of claim 5, wherein said lung disorder is selected from the group consisting of pulmonary hypertension (PH), COPD, asthma, acute lung injury, and radiation induced lung injury.

7. The method of claim 5, further comprising administering an additional treatment for a lung disorder.

8. The method of claim 7, wherein said additional treatment is selected from the group consisting of a vasodilator, an anticoagulant, an antiplatelet agent, an anti-inflammatory agent, and a vascular-remodeling therapy.

9. The method of claim 5, wherein said composition is administered to the lung of said subject using a dry powder inhaler.

* * * * *